(12) United States Patent
Gokel et al.

(10) Patent No.: US 10,791,740 B2
(45) Date of Patent: *Oct. 6, 2020

(54) ENHANCEMENT OF ANTIBIOTIC EFFICACY

(71) Applicant: The Curators of the University of Missouri, Columbia, MO (US)

(72) Inventors: George W. Gokel, Chesterfield, MO (US); Michael R. Gokel, Chesterfield, MO (US); Saeedeh Negin, St. Louis, MO (US); Mohit B. Patel, St. Louis, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/316,344

(22) PCT Filed: Jun. 5, 2015

(86) PCT No.: PCT/US2015/034550
§ 371 (c)(1),
(2) Date: Dec. 5, 2016

(87) PCT Pub. No.: WO2015/188140
PCT Pub. Date: Dec. 10, 2015

(65) Prior Publication Data
US 2017/0347652 A1 Dec. 7, 2017

Related U.S. Application Data

(60) Provisional application No. 62/008,956, filed on Jun. 6, 2014.

(51) Int. Cl.
*A61K 31/33* (2006.01)
*A61K 31/70* (2006.01)
(Continued)

(52) U.S. Cl.
CPC .......... *A01N 43/72* (2013.01); *A61K 31/165* (2013.01); *A61K 31/395* (2013.01);
(Continued)

(58) Field of Classification Search
CPC .. A61K 31/395; A61K 31/7008; A61K 31/65; A61K 31/43; A61K 9/127
(Continued)

(56) References Cited

U.S. PATENT DOCUMENTS 4,783,528 A 11/1988 Gokel
5,000,958 A * 3/1991 Fountain ................ A61K 9/127
424/417

(Continued)

FOREIGN PATENT DOCUMENTS

WO 2015/188140 A1 12/2015

OTHER PUBLICATIONS

Halwani et al. "Liposomal bismuth-ethanedithiol formulation enhances antimicrobial activity of tobramycin," International J. Pharmaceutics, 2008, vol. 358, pp. 278-284.*

(Continued)

*Primary Examiner* — Shengjun Wang
(74) *Attorney, Agent, or Firm* — Thompson Coburn LLP; William A. Holtz

(57) ABSTRACT

Methods and compositions are provided for increasing or enhancing the efficacy of antibiotics, such as by increasing antimicrobial activity, against a variety of microbes by co-administration with synthetic amphiphiles, including lariat ethers and hydraphiles. Methods and compositions for overcoming antibiotic resistance are also provided.

11 Claims, 13 Drawing Sheets

(51) Int. Cl.
| A61K 31/65 | (2006.01) |
| A01N 43/72 | (2006.01) |
| A61K 45/06 | (2006.01) |
| A61K 31/165 | (2006.01) |
| A61K 31/395 | (2006.01) |
| A61K 31/496 | (2006.01) |
| A61K 38/16 | (2006.01) |

(52) U.S. Cl.
CPC ............ *A61K 31/496* (2013.01); *A61K 31/65* (2013.01); *A61K 45/06* (2013.01); *A61K 38/16* (2013.01); *A61K 2300/00* (2013.01); *Y02A 50/473* (2018.01)

(58) Field of Classification Search
USPC ........... 514/183, 62, 154, 192, 199; 424/450
See application file for complete search history.

(56) References Cited

U.S. PATENT DOCUMENTS

| 8,389,505 | B2 | 3/2013 | Kralj et al. |
| 2002/0035061 | A1 | 3/2002 | Krieger et al. |
| 2009/0062221 | A1 | 3/2009 | Dow et al. |
| 2010/0222268 | A1 | 9/2010 | Hoffmann et al. |
| 2011/0257254 | A1 | 10/2011 | Kralj et al. |
| 2013/0224258 | A1 | 8/2013 | Baker |
| 2016/0361292 | A1 | 12/2016 | Gokel et al. |

OTHER PUBLICATIONS

Leevy et al. Correlation of bilayer membrane cation transport and biological activity in alkyl substituted lariat ethers, Org. Biomol. Chem. 2005, vol. 3, pp. 1647-1652. (Year: 2005).*

International Search Report and Written Opinion for PCT/US2015/34550 dated Aug. 26, 2015.

Gokel et al., "Lariat Ethers in Membranes and as Membranes", Bioorganic Chemistry Frontiers, 1990, pp. 115-141, vol. 1.

Leevy et al., "Synthetic Hydraphile Channels of Appropriate Length Kill *Escherichia coli*", Journal of the American Chemical Society, 2002, pp. 9022-9023, vol. 124.

Lomovskaya et al., "Identification and Characterization of Inhibitors of Multidrug Resistance Efflux Pumps in *Pseudomonas aeruginosa*: Novel Agents for Combination Therapy", Antimicrobial Agents and Chemotherapy, Jan. 2001, pp. 105-116, vol. 45, No. 1.

Mahamoud et al., "Antibiotic Efflux Pumps in Gram-Negative Bacteria: The Inhibitor Response Strategy", Journal of Antimicrobial Chemotherapy, 2007, pp. 1223-1229, vol. 59.

Murray et al., "Cation Flux Dependence on Carbon Chain Length in Hydraphile Channels as Assessed by Dynamic 23Na NMR Methods in Phospholipid Bilayers", Chemical Communications, 1998, pp. 2477-2478.

Murray et al., "Spacer Chain Length Dependence in Hydraphile Channels: Implications for Channel Position Within Phospholipid Bilayers", Journal of Supramolecular Chemistry, 2001, pp. 23-30, vol. 1.

Poole, "Efflux-Mediated Multiresistance in Gram-Negative Bacteria", Clinical Microbiology and Infection, Jan. 2004, pp. 12-26, vol. 10, No. 1.

Weber et al., "Dynamic Assessment of Bilayer Thickness by Varying Phospholipid and Hydraphile Synthetic Channel Chain Lengths", Journal of the Ameican Chemical Society, 2005, pp. 636-642, vol. 127.

Office Action for U.S. Appl. No. 15/186,070, dated Nov. 3, 2017.

Poole, "Efflux Pumps as Antimicrobial Resistance Mechanisms", Annals of Medicine, 2007, pp. 162-176, vol. 39(3).

Schlecht et al., "Overview of Antibacterial Drugs", Merck Manual, Professional Version, Jan. 2005.

* cited by examiner

ENHANCEMENT OF ANTIBIOTIC EFFICACY

CROSS-REFERENCE TO RELATED APPLICATIONS

This application is a U.S. National Phase application of PCT/US2015/034550, filed on Jun. 5, 2015, which claims the benefit of U.S. Provisional Application No. 62/008,956 filed Jun. 6, 2014 both of which are hereby incorporated by reference in their entireties.

STATEMENT OF FEDERALLY SPONSORED RESEARCH

This invention was made with Government support under CHE 1307324 awarded by the National Science Foundation. The Government has certain rights in the invention.

BACKGROUND

Certain synthetic amphiphiles are known to exhibit toxicity to microbes such as Gram negative *Escherichia coli*, Gram positive *Bacillus subtilis*, and the yeast *Saccharomyces cerevisiae*. The minimum inhibitory concentrations (MICs) of such synthetic amphiphiles against the various microbes depend on the microbe per se and on the structure of the synthetic amphiphile.

Combination drugs such as amoxicillin and clavulanic acid, sold as AUGMENTIN®, and piperacillin and tazobactam, sold as ZOSYN®, are effective antimicrobials. Certain amphiphilic calixarene molecules have been prepared with integral antibiotic elements, but these comprise prodrugs rather than combination therapies as described in *Bioorganic and Medicinal Chemistry* 2012, 20, 2035-2041.

There still remains a need to identify composition and methods to enhance antimicrobial activity of current antimicrobial agents and to combat increasing microbe resistance to antibiotics.

SUMMARY

Disclosed herein are various embodiments of a method of enhancing the antimicrobial activity of an antibiotic. In certain embodiments, a method comprises administering to a microbe the antibiotic with a synthetic amphiphile. In certain embodiments, the synthetic amphiphile is a compound comprising one or more polar head groups in which each polar head group comprises at least three oxygen and hydrocarbon residues as the nonpolar elements. In certain embodiments, the synthetic amphiphile is a lariat ether or a hydraphile. In certain embodiments, the antibiotic and synthetic amphiphile are administered to the microbe such as by contacting the microbe in culture or in solution or by applying the antibiotic and synthetic amphiphile to a material, such as the surface of a material, in or on which the microbe resides. In certain embodiments, the method increases the antimicrobial activity of the antibiotic by about 2-fold to about 40-fold.

In certain embodiments, the synthetic amphiphile is a lariat ether. In certain embodiments, the synthetic amphiphile is a lariat ether and the lariat ether comprises a diaza-18-crown-6 macrocycle and two linear alkyl chains ranging in length from 1 to 20 carbon atoms, or from 1 to 22 carbon atoms. In certain embodiments, the synthetic amphiphile is a lariat ether and the lariat ether comprises a diaza-15-crown-5 macrocycle and two linear alkyl chains ranging in length from 1 to 20 carbon atoms, or from 1 to 22 carbon atoms. In certain embodiments, the synthetic amphiphile is a lariat ether and the lariat ether is N,N'-di-n-octyl-4,13-diaza-18-crown-6. In certain embodiments, the synthetic amphiphile is a lariat ether and the lariat ether is N,N'-di-n-decyl-4,13-diaza-18-crown-6. In certain embodiments, the synthetic amphiphile is a lariat ether and the lariat ether is N,N'-di-n-undecyl-4,13-diaza-18-crown-6. In certain embodiments, the synthetic amphiphile is a lariat ether and the lariat ether is N,N'-di-n-dodecyl-4,13-diaza-18-crown-6. In certain embodiments, the synthetic amphiphile is a lariat ether and the lariat ether is N,N'-di-n-tetradecyl-4,13-diaza-18-crown-6. In certain embodiments, the synthetic amphiphile is a lariat ether and the lariat ether does not comprise an adamantyl group.

In certain embodiments, the synthetic amphiphile is a hydraphile. In certain embodiments, the synthetic amphiphile is a hydraphile and the hydraphile comprises the structure of Formula 4:

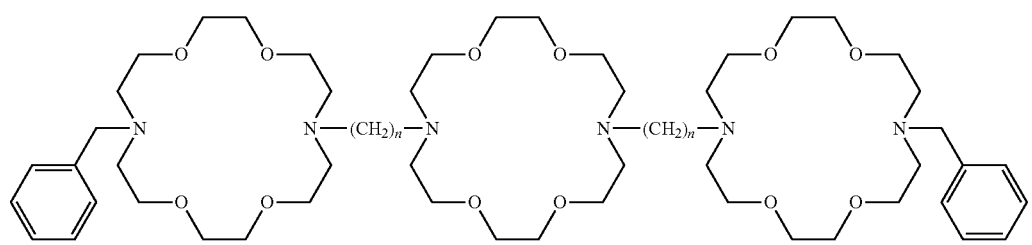

Formula 4 wherein n is 6. In certain embodiments, the synthetic amphiphile is a hydraphile and the hydraphile comprises the structure of Formula 4:

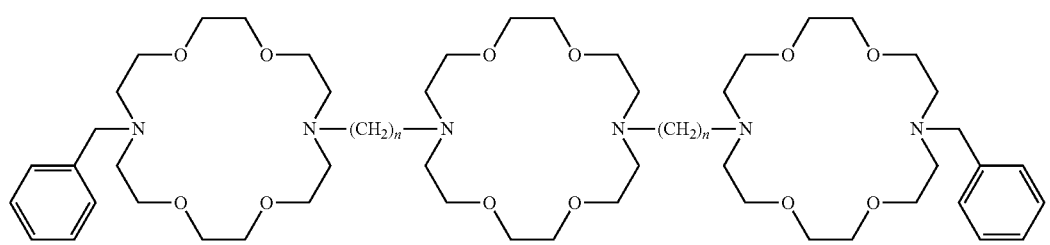

Formula 4 wherein n is 8. In certain embodiments, the synthetic amphiphile is a hydraphile and the hydraphile comprises the structure of Formula 4:

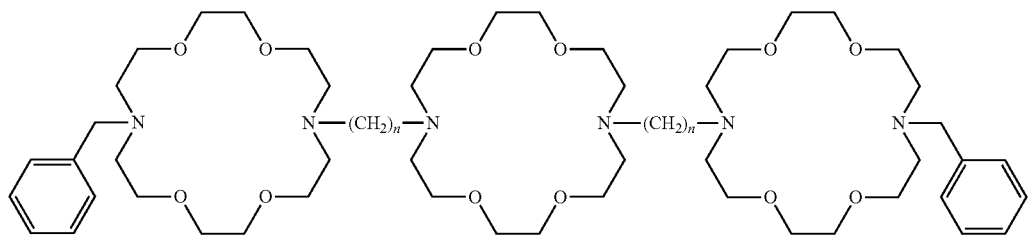

Formula 4 wherein n is 10. In certain embodiments, the synthetic amphiphile is a hydraphile and the hydraphile comprises the structure of Formula 2:

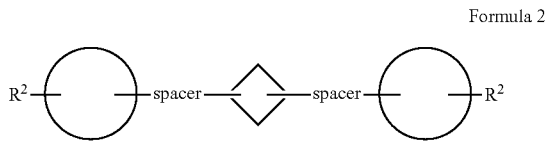

Formula 2 wherein the macrocycles (open circles) are 4,10-diaza-15-crown-5, the spacers are n-dodecylene, and the side chains ($R^2$) are n-dodecyl. The diamond (middle between spacers) represents a polar structural element. In certain embodiments, the polar structural element is a macrocycle. Compounds 3 and 7 as shown in FIG. 10 are representative hydraphiles in which the polar element is not a macrocycle but rather a triethyleneoxy unit or an amide-containing module.

In certain embodiments, the microbe is a bacterium. In certain embodiments, the microbe is a bacterium in the family Enterobacteriaceae, in the family Bacillaceae, or in the family Pseudomonadaceae. In certain embodiments, the bacterium is *Escherichia coli* (*E. coli*). In certain embodiments, the microbe is a bacterium that is resistant to the antibiotic. In certain embodiments, the bacterium is an antibiotic resistant *E. coli*.

In the present context, antibacterial and antimicrobial are understood to mean any compound that either inhibits or completely arrests or prevents microbial growth or kills the microbe.

In certain embodiments, the antibiotic, the synthetic amphiphile, or both the antibiotic and the synthetic amphiphile are administered at a concentration below their minimum inhibitory concentrations. In certain embodiments, the antibiotic is administered at a concentration below its minimum inhibitory concentration. In certain embodiments, the synthetic amphiphile is administered at a concentration below its minimum inhibitory concentration. In certain embodiments, both the antibiotic and the synthetic amphiphile are administered at concentrations below their minimum inhibitory concentrations when determined in the absence of the second additive. In certain embodiments, the antibiotic is administered to a concentration of about 0.1 µM to about 400 µM. In certain embodiments, the synthetic amphiphile is administered to a concentration of about 0.1 µM to about 400 µM. In certain embodiments, the antibiotic is administered to a concentration of about 0.1 µM to about 400 µM and the synthetic amphiphile is administered to a concentration of about 0.1 µM to about 400 µM.

In certain embodiments, the antibiotic is an antibiotic selected from the group consisting of kanamycin, tobramycin, erythromycin, rifampicin, and tetracycline. In certain embodiments, the antibiotic is an antibiotic selected from the group consisting of erythromycin, rifampicin, and tetracycline. In certain embodiments, the antibiotic is kanamycin. In certain embodiments, the antibiotic is tobramycin. In certain embodiments, the antibiotic is erythromycin. In certain embodiments, the antibiotic is rifampicin. In certain embodiments, the antibiotic is tetracycline.

In certain embodiments, the microbe is *E. coli*, the antibiotic is selected from the group consisting of rifampicin, tetracycline, kanamycin, and erythromycin, and the synthetic amphiphile is N,N'-di-n-octyl-4,13-diaza-18-crown-6 lariat ether or N,N'-di-n-undecyl-4,13-diaza-18-crown-6 lariat ether. In certain embodiments, the microbe is a tetracycline resistant strain of *E. coli*, the antibiotic is tetracycline, and the synthetic amphiphile is a hydraphile.

Certain embodiments provide for methods of treating a microbial infection. Such methods comprise administering to a subject suffering from the microbial infection an effective amount of a combination of an antibiotic and a synthetic amphiphile as described herein.

DETAILED DESCRIPTION

It is to be noted that the term "a" or "an" entity refers to one or more of that entity; for example, "an antibiotic" is understood to represent one or more antibiotics. As such, the terms "a" (or "an"), "one or more," and "at least one" can be used interchangeably herein.

Unless defined otherwise, all technical and scientific terms used herein have the same meaning as commonly understood by one of ordinary skill in the art to which this disclosure is related.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole.

It has been discovered that the combination of certain synthetic amphiphiles with a range of antimicrobial agents, such as antibiotics, shows unexpectedly enhanced efficacy, increased activity, etc., of the antimicrobial agents against a range of organisms, including in some cases those microbes that are resistant to a particular antimicrobial agent. It has further been discovered that certain hydraphiles that are too) short to form ion-conducting channels surprisingly and unexpectedly also enhanced antimicrobial activity. It was also discovered that organisms that are resistant to certain antimicrobial agents succumb to that antimicrobial agent when the antimicrobial agent and one or more synthetic amphiphiles, such as those described herein, is co-administered with the antimicrobial agent.

Lariat ethers are compounds known in the art as cation complexing agents such as described in U.S. Pat. Nos. 4,436,664, 4,474,963, 4,597,903, and 4,687,844. Lariat ethers contain a macrocyclic ring and one or more sidearms as described herein. A macrocycle is a ring compound comprising at least 9-members, but more typically 12 or more atoms connected together. Macrocyclic rings at least as large as 60 atoms are also known in the art. Lariat ethers are characterized by a macrocyclic ring having from 12-48 members and containing heteroatoms including, but not limited to, oxygen, nitrogen and sulfur. Lariat ethers possess one or more side arms or side chains attached to the macrocyclic ring. The attachment of the side chains can be at carbon, nitrogen, or sulfur or any combination thereof within the ring. Heteroatoms such as oxygen, nitrogen, and sulfur can also be present in the side arms. The side arms can be linear or branched alkyl, unsaturated alkyl, aralkyl, aryl, or heteroaryl, and heteroatoms such as oxygen, nitrogen, and/or sulfur can be present in or attached to the aralkyl, aryl, or heteroaryl portions of the side chains. Lariat ethers are known to be amphiphiles as described in *Advances in Bio-organic Frontiers*; H. Dugas, Springer Verlag: Berlin. 1990; Vol. 1; pp 116-141.

Figure 10:
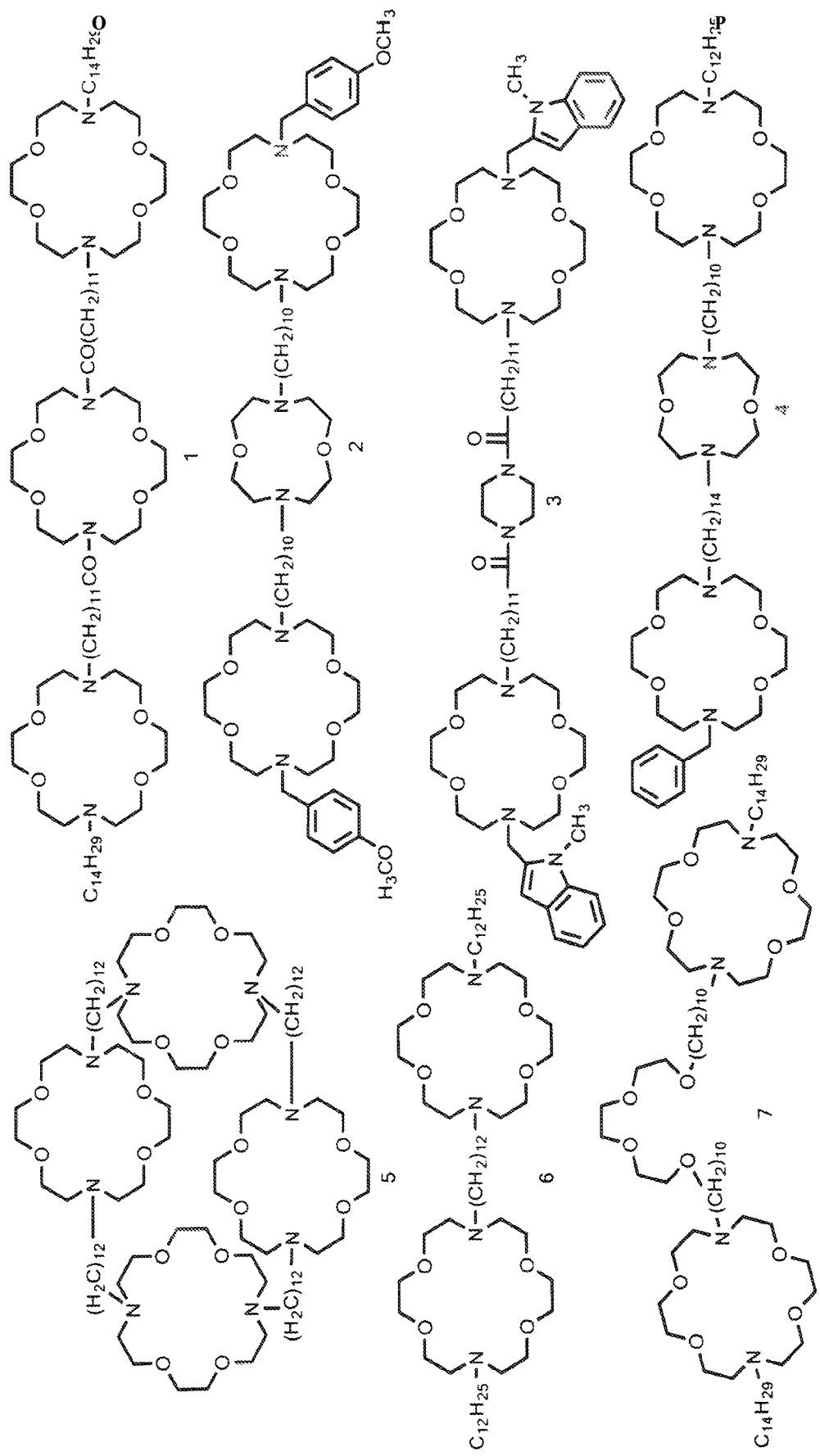
FIG. 10 shows seven representative examples of chemical structures of hydraphiles and hydraphile-like compounds.

Hydraphiles are synthetic amphiphiles known in the art such as described in *Chemical Communications* 2000, 1-9. Hydraphiles are typically composed of three macrocyclic rings, separated by organic spacer elements, and terminated by various side arms. In certain embodiments, the side arm can be hydrogen attached to a nitrogen heteroatom. The spacer chains can contain 1-30 carbon atoms and can be saturated or unsaturated, linear or branched, including aromatic and heteroaromatic. The side arms can be linear or branched alkyl, unsaturated alkyl, aralkyl, aryl, or heteroaryl and the spacer chains can contain heteroatoms such as oxygen, nitrogen, and/or sulfur. Hydraphiles have also been prepared that have two (e.g., 3, 7) and four (e.g., 5) macrocyclic rings that function as pore-formers in bilayer membranes as shown in FIG. 10.

Figure 11:
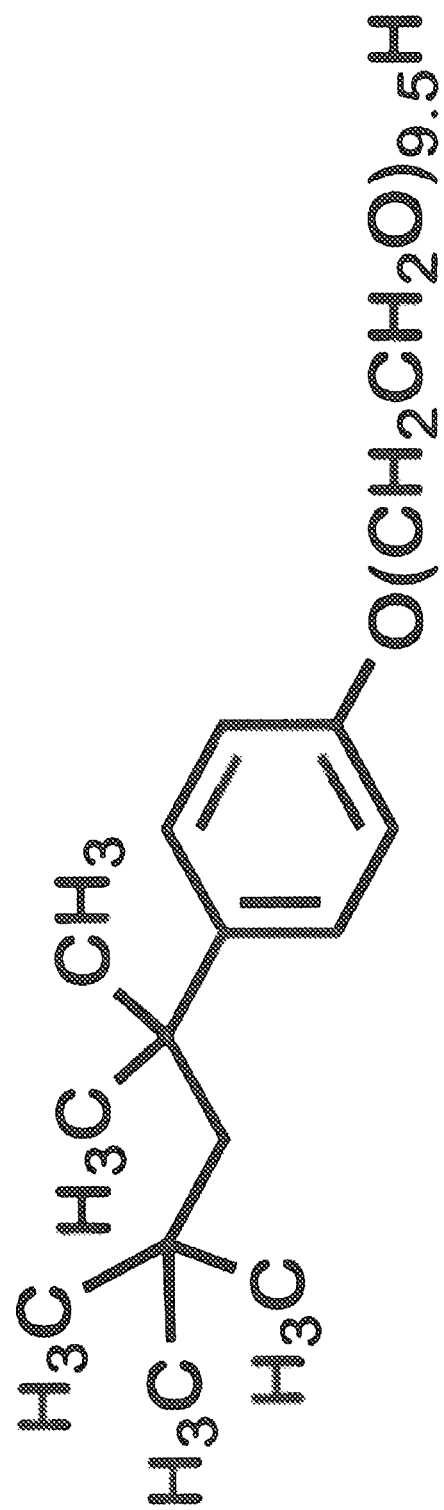
FIG. 11 shows the chemical structure of TRITON X-100.

Amphiphiles are compounds that have both polar and non-polar elements. A synthetic amphiphile as understood herein is a compound that contains at least one polar element or "head group" and at least one nonpolar element or "tail." TRITON X-100, shown in FIG. 11, is one representative example. The compound numbered 7 in FIG. 10 is another representative example and has two polar macrocycles and a triethyleneoxy group that can also serve as a polar head group.

Figure 1:
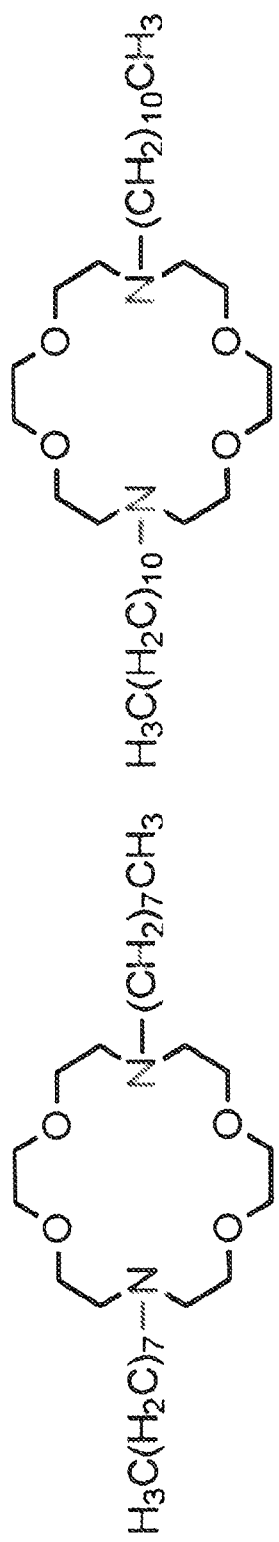
FIG. 1 illustrates chemical structures of N,N'-di-n-octyl-4,13-diaza-18-crown-6 and N,N'-di-n-undecyl-4,13-diaza-18-crown-6, which are exemplified in the present disclosure.

An example of a synthetic amphiphile is the detergent sold as TRITON X-100 (FIG. 11) in which the hydrocarbon residue is nonpolar and the oligoethylene glycol portion is polar. Certain embodiments are directed to synthetic amphiphiles such as, but not limited to, N,N'-di-n-undecyl-4,13-diaza-18-crown-6. In this compound, the 18-membered macrocyclic ring possesses six heteroatoms (four oxygens and two nitrogens) that render the cyclic structure polar. The two 11-carbon chains attached to the two macrocyclic ring nitrogen atoms are hydrophobic and nonpolar and comprise the synthetic amphiphile's nonpolar elements. FIG. 1 is an illustrative example showing the chemical structures of N,N'-bis(n-octyl)-4,13-diaza-18-crown-6 and N,N'-bis(n-undecyl)-4,13-diaza-18-crown-6. It is understood, however, that the methods described herein are not limited to the synthetic amphiphiles illustrated in FIG. 1.

Certain aspects are drawn to a method for increasing or enhancing the antimicrobial activity of an antimicrobial agent. As used herein, the "antimicrobial activity" of an antimicrobial agent is defined as the property of a substance to inhibit the growth and reproduction of a microbial organism or to kill it. Common terms generally applied to bacteria are bacteriostatic (stops growth) and bactericidal (kills bacteria). Depending on the concentrations applied, microbial growth can be slowed or stopped in comparison to concurrent experiments conducted in the absence of an antimicrobial agent. Depending on the concentrations applied, additional microbe death can occur in comparison to concurrent experiments conducted in the absence of an antimicrobial agent. The results of minimum inhibitory concentration (MIC) evaluations and growth curves are presented herein and the conditions are specified. The MIC is the lowest concentration of any agent having antimicrobial activity that inhibits the growth of a microorganism as judged by visual inspection. MIC can be determined by inoculating media with the organism and adding the antimicrobial agent diluted successively in half. After an appropriate incubation time, the MIC is evaluated by inspection as the transition between two successive 2-fold dilutions in which the one concentrated sample is clear and growth is apparent in the 2-fold less concentrated sample. Reference herein to increasing or enhancing activity, efficacy, potency, and the like are used interchangeably to mean that when the synthetic amphiphile is present, the ability of the antimicrobial agent to inhibit the growth of or to kill an organism will be manifested at a concentration lower than would be required to achieve the same results in the absence of said synthetic amphiphile. In certain embodiments, the method increases the antimicrobial activity of the antibiotic by: about 2-fold to about 40-fold; by about 5-fold to about 40-fold; by about 10-fold to about 40-fold; by about 15-fold to about 40-fold; by about 20-fold to about 40-fold; by about 25-fold to about 40-fold; by about 30-fold to about 40-fold, by about 35-fold to about 40-fold; or by about 40-fold. In certain embodiments, the method increases the antimicrobial activity of the antibiotic; by about 2-fold to about 48-fold; by about 5-fold to about 48-fold; by about 10-fold to about 48-fold; by about 15-fold to about 48-fold; by about 20-fold to about 48-fold; by about 25-fold to about 48-fold; by about 30-fold to about 48-fold; by about 35-fold to about 48-fold; by about 40-fold to about 48-fold; or by about 48-fold. In certain embodiments, the method increases the antimicrobial activity of the antibiotic; by about 2-fold to about 50-fold; by about 5-fold to about 50-fold; by about 10-told to about 50-fold; by about 15-fold to about 50-fold; by about 20-fold to about 50-fold; by about 25-fold to about 50-fold; by about 30-fold to about 50-fold; by about 35-fold to about 50-fold; by about 40-fold to about 50-fold; by about 50-fold, or greater than about 50-fold.

Figure 2:
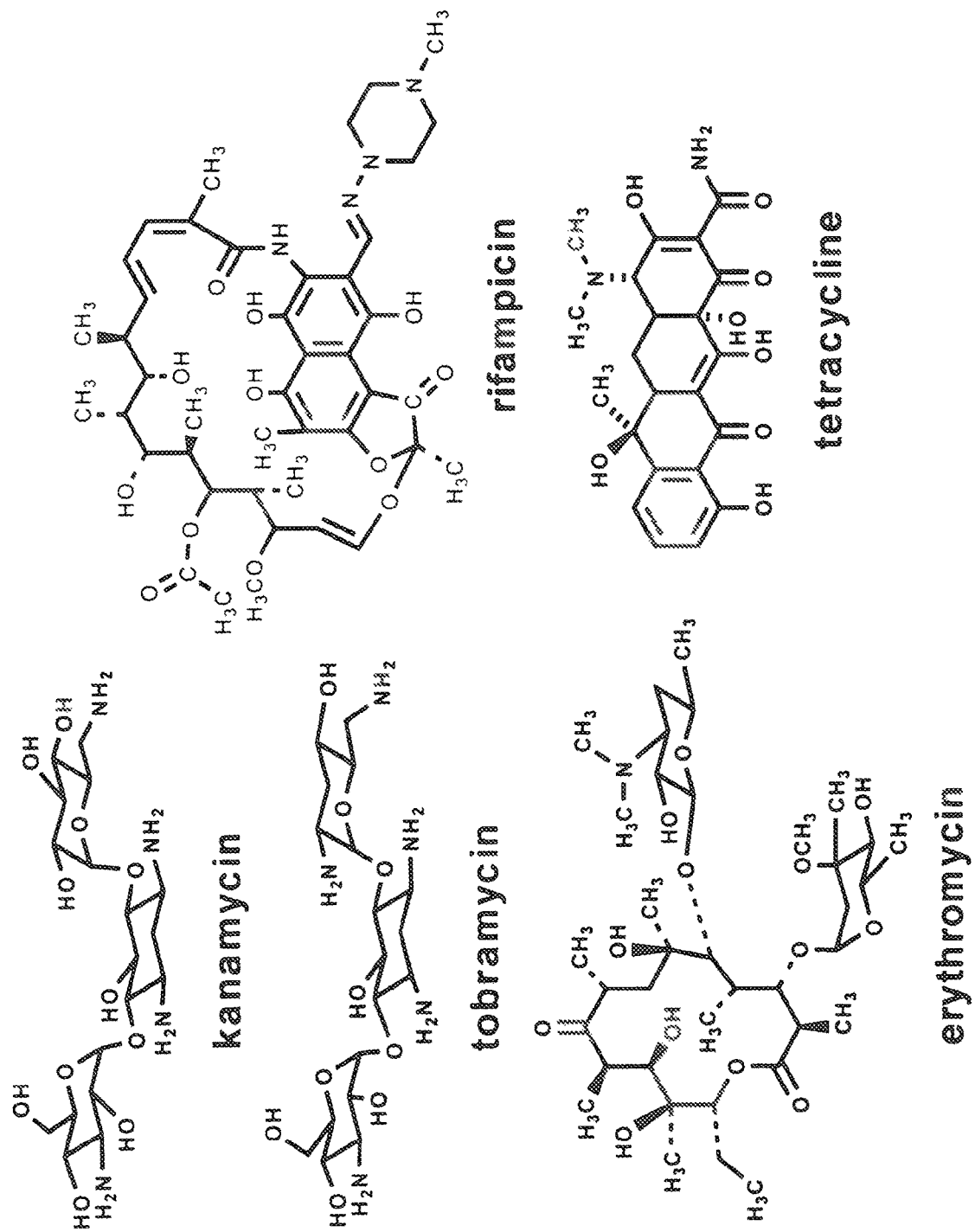
FIG. 2 illustrates chemical structures of five antibiotics that are exemplified in the present disclosure.

In certain embodiments, the antimicrobial agent is an antibiotic. The structures of five illustrative antibiotics are shown in FIG. 2 (i.e., kanamycin, tobramycin, erythromycin, rifampicin, and tetracycline). It is understood that the methods described herein are not limited to the antibiotics illustrated in FIG. 2. Other antibiotics are exemplified herein and numerous other antibiotics, too numerous to list, are contemplated. For example, the following is a brief list of some compounds that are within the scope of the disclosure: Carbapenems such as Imipenem, Meropenem, Ertapenem, Doripenem, and Biapenem; penicillins, cephalosporins (Cefoxitin), glycopeptides (vancomycin), macrolides (azithromycin, clarithromycin), quinolones (ciprolloxacin, naldixic acid), sulfamides (sulfadiazine), isoniazid, and streptomycin. In certain embodiments, the antibiotic is administered to a concentration of:

about 0.001 µM to about 400 µM;
about 0.001 µM to about 300 µM;
about 0.001 µM to about 200 µM;
about 0.001 µM to about 100 µM;
about 0.001 µM to about 50 µM;
about 0.001 µM to about 25 µM;
about 0.001 µM to about 10 µM;
about 0.001 µM to about 1 µM;
about 0.001 µM to about 0.1 µM; or
about 0.001 µM to about 0.01 µM.

In certain embodiments, the antibiotic is administered to a concentration of:

about 0.01 µM to about 400 µM;
about 0.01 µM to about 300 µM;
about 0.01 µM to about 200 µM;
about 0.01 µM to about 100 µM;
about 0.01 µM to about 50 µM;
about 0.01 µM to about 25 µM;
about 0.01 µM to about 10 µM;
about 0.01 µM to about 1 µM; or
about 0.01 µM to about 0.1 µM.

In certain embodiments, the antibiotic is administered to a concentration of:

about 0.1 µM to about 400 µM;
about 0.1 µM to about 300 µM;
about 0.1 µM to about 200 µM;
about 0.1 µM to about 100 µM;
about 0.1 µM to about 50 µM;
about 0.1 µM to about 25 µM;
about 0.1 µM to about 10 µM; or
about 0.1 µM to about 1.0 µM.

In certain embodiments, the antibiotic is administered to a concentration of:

about 0.001 µM to about 400 µM;
about 0.01 µM to about 400 µM;
about 0.1 µM to about 400 µM;
about 1.0 µM to about 400 µM;
about 10 µM to about 400 µM;
about 100 µM to about 400 µM;
about 200 µM to about 400 µM;
about 300 µM to about 400 µM;
about 0.001 µM to about 300 µM;
about 0.01 µM to about 300 µM;
about 0.1 µM to about 300 µM;
about 1.0 µM to about 300 µM;
about 10 µM to about 300 µM;
about 100 µM to about 300 µM;
about 200 µM to about 300 µM;
about 0.001 µM to about 200 µM;
about 0.01 µM to about 200 µM;
about 0.1 µM to about 200 µM;
about 1.0 µM to about 200 µM;
about 10 µM to about 200 µM;
about 100 µM to about 200 µM;
about 0.001 µM to about 100 µM;
about 0.01 µM to about 100 µM;
about 0.1 µM to about 100 µM;
about 1.0 µM to about 100 µM;
about 10 µM to about 100 µM; or
about 50 µM to about 100 µM.

Certain aspects are drawn to a method for increasing or enhancing the antimicrobial activity of an antimicrobial agent by administering the antimicrobial agent in combination with a synthetic amphiphile. In certain embodiments, the synthetic amphiphile that is capable of increasing or enhancing antimicrobial activity is a lariat ether and/or a hydraphile. In certain embodiments, a synthetic amphiphile is capable of reversing the resistance of a microbe to an antimicrobial agent. In certain embodiments, the synthetic amphiphile that is capable of reversing the resistance of a microbe to an antimicrobial agent is a lariat ether and/or a hydraphile. In certain embodiments, the synthetic amphiphile is administered to a concentration of:

about 0.001 µM to about 400 µM;
about 0.001 µM to about 300 µM;
about 0.001 µM to about 200 µM;
about 0.001 µM to about 100 µM;
about 0.001 µM to about 50 µM;
about 0.001 µM to about 25 µM;
about 000.1 µM to about 10 µM;
about 0.001 µM to about 1 µM;
about 0.001 µM to about 0.1 µM; or
about 0.001 µM to about 0.01 µM.

In certain embodiments, the synthetic amphiphile is administered to a concentration of:

about 0.01 µM to about 400 µM;
about 0.01 µM to about 300 µM;
about 0.01 µM to about 200 µM;
about 0.01 µM to about 100 µM;
about 0.01 µM to about 50 µM;
about 0.01 µM to about 25 µM;
about 0.01 µM to about 10 µM;
about 0.01 µM to about 1 µM; or
about 0.01 µM to about 0.1 µM.

In certain embodiments, the synthetic amphiphile is administered to a concentration of:
about 0.1 µM to about 400 µM;
about 0.1 µM to about 300 µM;
about 0.1 µM to about 200 µM;
about 0.1 µM to about 100 µM;
about 0.1 µM to about 50 µM;
about 0.1 µM to about 25 µM;
about 0.1 µM to about 10 µM; or
about 0.1 µM to about 1.0 µM.

In certain embodiments, the synthetic amphiphile is administered to a concentration of:
about 0.001 µM to about 400 µM;
about 0.01 µM to about 400 µM;
about 0.1 µM to about 400 µM;
about 1.0 µM to about 400 µM;
about 10 µM to about 400 µM;
about 100 µM to about 400 µM;
about 200 µM to about 400 µM;
about 300 µM to about 400 µM;
about 0.001 µM to about 300 µM;
about 0.01 µM to about 300 µM;
about 0.1 µM to about 300 µM;
about 1.0 µM to about 300 µM;
about 10 µM to about 300 µM;
about 100 µM to about 300 µM;
about 200 µM to about 300 µM;
about 0.001 µM to about 200 µM;
about 0.01 µM to about 200 µM;
about 0.1 µM to about 200 µM;
about 1.0 µM to about 200 µM;
about 10 µM to about 200 µM;
about 100 µM to about 200 µM;
about 0.001 µM to about 100 µM;
about 0.01 µM to about 100 µM;
about 0.1 µM to about 100 µM;
about 1.0 µM to about 100 µM;
about 10 µM to about 100 µM; or
about 50 µM to about 100 µM.

It is understood that in certain embodiments, the antibiotic and the synthetic amphiphile can be administered together to the respective concentrations disclosed herein.

Figure 12:
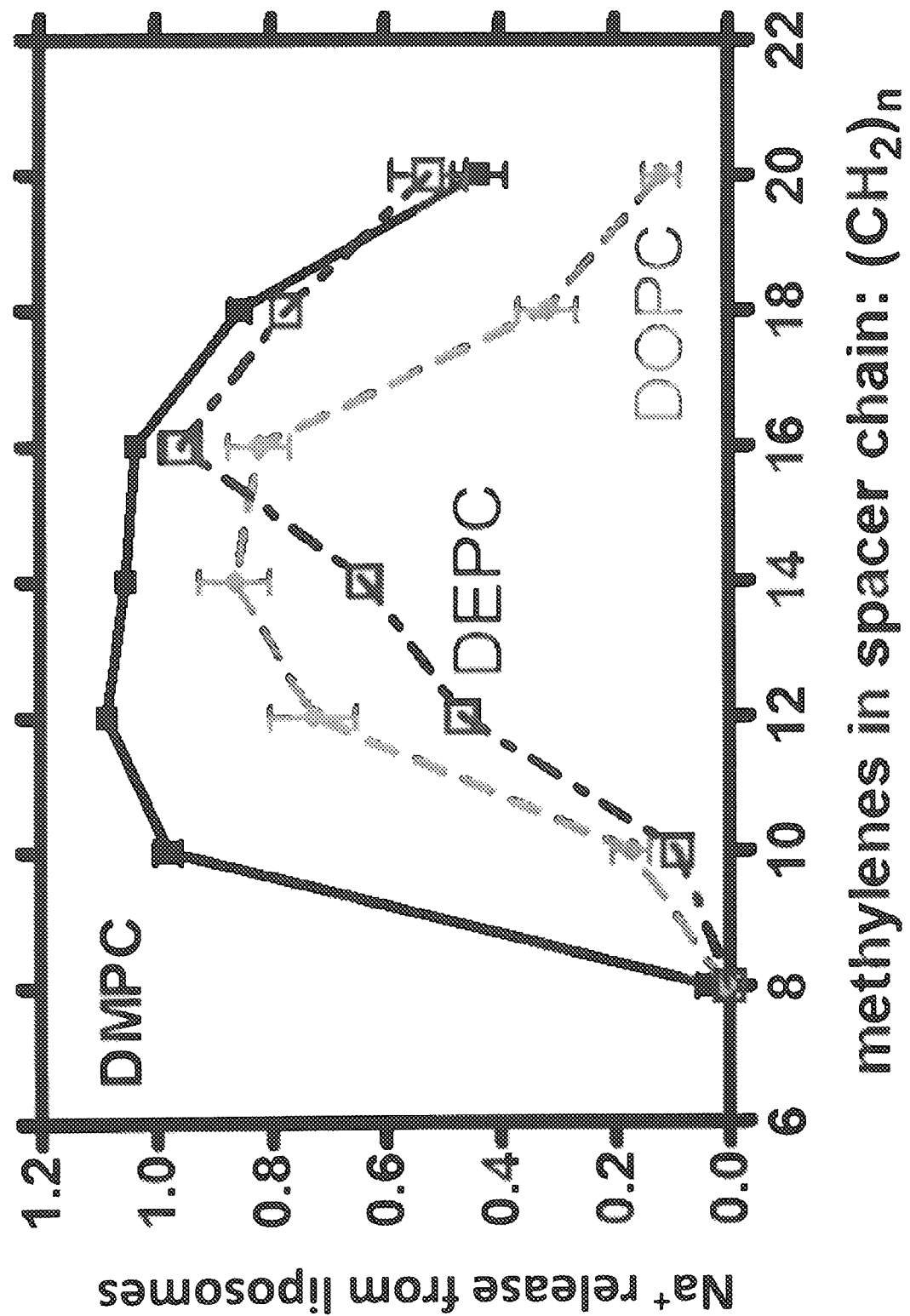
FIG. 12 shows the correspondence between membrane thickness and hydraphile spacer chain length as determined by the percentage of ions released from vesicles.

In certain embodiments, a short-chain hydraphile is used to increase or enhance the potency or antimicrobial activity of an antimicrobial agent. In certain embodiments, a short-chain hydraphile is used to reverse the resistance of a microbe to an antimicrobial agent. Short-chained hydraphiles have spacer chains of such a length that they do not span the lipid bilayer and therefore do not exhibit the property of cation transport by pore formation. The length dependence was demonstrated in *Chemical Communications* 1998, 2477-2478. However, it is well known in the art that the membranes of cells have many different components and thicknesses. It was demonstrated in the *Journal of the American Chemical Society* 2005, 126, 636-642, that the ability of hydraphiles to transport cations depended on the correspondence between membrane thickness and hydraphile spacer chain length. Thus, liposomes were formed from three different phospholipids: 1,2-dimyristoleoyl-sn-glycero-3-phosphocholine (DMPC, shorter fatty acid chains, thinner membranes), 1,2-dioleoyl-sn-glycero-3-phosphocholine (DOPC), and 1,2-dierucoyl-sn-glycero-3-phosphocholine (DEPC, longest fatty acid chains, thickest membranes). The graph of FIG. 12 shows that $C_8$ benzyl hydraphile failed to transport irrespective of whether it was present in DMPC, DOPC, or DEPC membranes. The $C_8$ benzyl hydraphile is a short-chained hydraphile and those compounds having spacer chains shorter than eight linear atoms can also be classified as short-chained hydraphiles. The graph of FIG. 12 also shows that in the thickest DEPC membranes, $C_{10}$ benzyl hydraphile is nearly inactive. Thus, short-chained hydraphiles are those that fail to transport cations by pore formation in the context of the organism's membrane structure. It is known from the *Journal of the American Chemical Society* 2002, 124, 9022-3, that hydraphiles are toxic to *E. coli* in appropriate concentrations. Thus, $C_{12}$ benzyl hydraphile killed *E. coli* but $C_8$ benzyl hydraphile did not.

As used herein, a short-chained hydraphile comprises spacer chains of such a length that they do not span the lipid bilayer of a particular membrane to which the short-chained hydraphiles are contacted and therefore do not exhibit the property of cation transport by pore formation. In certain embodiments, a short-chained hydraphile has spacer chains of ten or less linear atoms. In certain embodiments, a short-chained hydraphile has spacer chains of eight or less linear atoms. In certain embodiments, a short-chained hydraphile has spacer chains of six or less linear atoms.

A general formula for lariat ethers is shown as Formula 1.

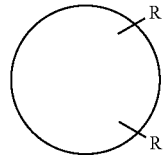

Formula 1

In Formula 1, the circle represents a macrocyclic ring, which can be composed of heteroatoms such as O, N, and/or S. The ring sizes can range from about 12 members to about 48 members. The side arms (R) can be saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues. In certain of any of the embodiments disclosed herein, a lariat ether does not comprise an adamantyl group. In certain of any of the embodiments disclosed herein, an adamantyl group is not incorporated as a terminal residue in a side chain or the side chains of a lariat ether of the embodiments.

A general formula for hydraphiles is shown as Formula 2.

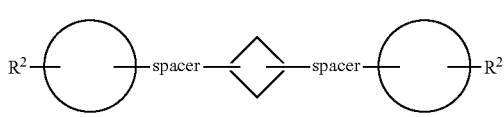

Formula 2

The spacers (also referred to as "spacer chains") can range from 1-30 atoms and can be linear or branched, and can be saturated or unsaturated. The size of the macrocyclic rings can range from about 12 members to about 48 members. The side arms ($R^2$) can be linear or branched, saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues. The diamond (middle between spacers) represents a polar structural element. In certain embodiments, the polar structural element is a macrocycle. Compounds 3 and 7 as shown in FIG. 10 are representative hydraphiles in which the polar element is not a macrocycle but rather a triethyleneoxy unit or an amide-containing module.

A more specific illustrative example of a lariat ether is the structure shown in Formula 3, where n has values from about 0 to about 16, or from about 4 to about 16, and $R^1$ is described below.

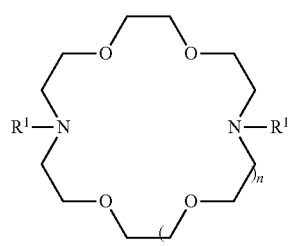

Formula 3

Lariat ethers similar to Formula 3 but having 12-membered macrocyclic rings are also provided for.

Figure 3:
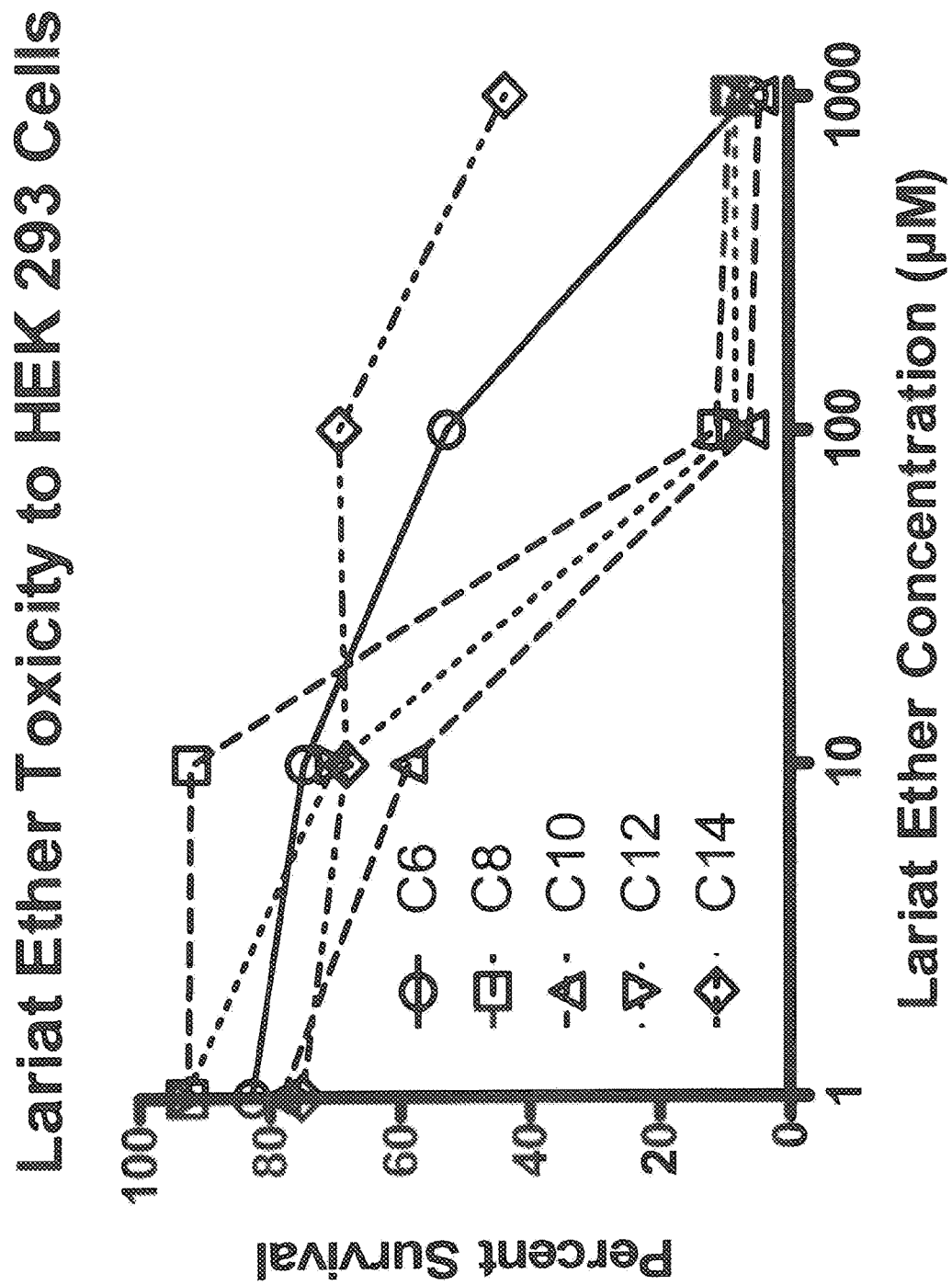
FIG. 3 is a graphical representation of lariat ether toxicity to HEK 293 cells.

The side arms ($R^1$) of lariat ethers can be linear or branched alkyl, unsaturated alkyl, aralkyl, or aryl, or heteroaryl. When the value of "n" in the structure of FIG. 3 is 1, the macrocyclic ring is 4,13-diaza-18-crown-6. When $R^1$ is saturated alkyl, the side chains can be methyl, ethyl, normal alkyl from n-propyl to n-eiscosanyl (also called n-icosanyl) or branched chain isomers thereof. The corresponding branched chain isomers and/or unsaturated derivatives are also contemplated as are various ring sizes and heteroatom compositions including, but not limited to, O, N, and S. Non-limiting illustrative examples of lariat ethers include: diaza-18-crown-6 macrocycle with two linear alkyl chains ranging in length from 1 to 20 carbon atoms, or from 1 to 22 carbon atoms; diaza-15-crown-5 macrocycle with two linear alkyl chains ranging in length from 1 to 20 carbon atoms, or from 1 to 22 carbon atoms; N,N'-di-n-octyl-4,13-diaza-18-crown-6; N,N'-di-n-decyl-4,13-diaza-18-crown-6; N,N'-di-n-undecyl-4,13-diaza-18-crown-6; N,N'-di-n-dodecyl-4,13-diaza-18-crown-6; and N,N'-di-n-tetradecyl-4,13-diaza-18-crown-6. A representative example of a lariat ether having a more complex structure is the compound shown as 6 in FIG. 10. Compound 6 in FIG. 10 can also be described as a bolaamphiphile.

Formula 2 above shows a generalized structure for the compounds known as hydraphiles. In Formula 2. $R^2$ are the aforementioned side arms and the term "spacer" designates the linkage units that covalently connect the macrocyclic rings.

A more specific illustrative example of a hydraphile is the structure shown in Formula 4, where n is the number of methylene groups from 1-30.

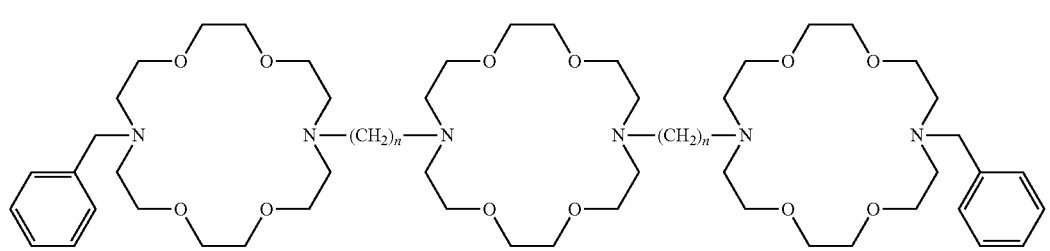

Formula 4

Some non-limiting illustrative examples of hydraphiles include: the structure of Formula 4:

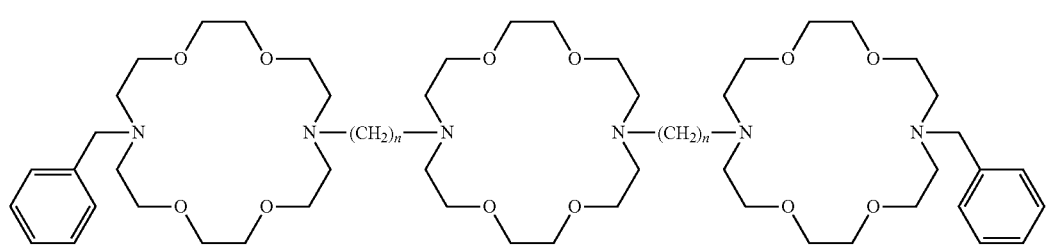

Formula 4 wherein n is 6; the structure of Formula 4:

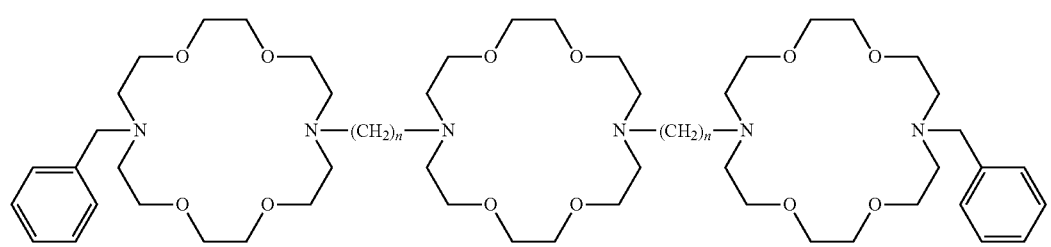

Formula 4 wherein n is 8; the structure of Formula 4:

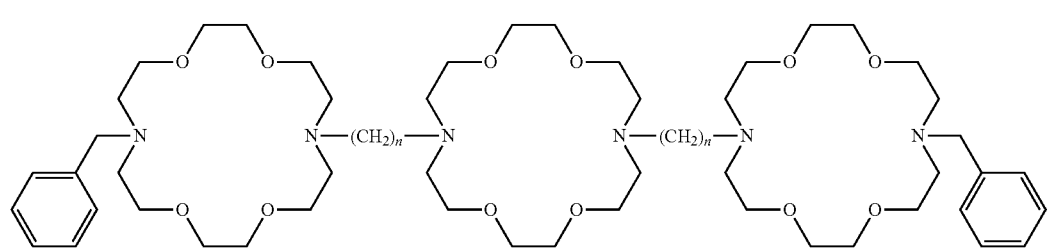

Formula 4 wherein n is 10, 12, 14, or 16; and the structure of Formula 2:

Formula 2

$R^2$—⊙—spacer—◇—spacer—⊙—$R^2$ wherein the macrocycles (open circles) are 4,10-diaza-15-crown-5, the spacers are n-dodecylene, and the side chains ($R^2$) are n-dodecyl, and the diamond is 4,10-diaza-15-crown-5. Represented another way, in certain embodiments, the structure can be $R^2$—X—S—Y—S—X—$R^2$: wherein X (the macrocycles) can be 4,10-diaza-15-crown-5. S (spacers) can be n-dodecylene, $R^2$ (side chains) can be n-dodecyl, and Y (polar structural element) can be 4,10-diaza-15-crown-5.

Certain aspects are drawn to the administration of synthetic amphiphiles with antimicrobial agents. In certain embodiments, the synthetic amphiphile is a lariat ether or a hydraphile. A combination of the antimicrobial agent and the synthetic amphiphile can be administered by any route, protocol, means, etc., appropriate for its administration and embodiments are not limited to any particular route, protocol, means. etc. of administration. For example, the antibiotic and synthetic amphiphile can be administered to the microbe such as by contacting the microbe in culture or in solution or by applying the antibiotic and synthetic amphiphile to a material, such as the surface of a material, in or on which the microbe resides. Administration can be to a subject having a microbial infection and such administration to the subject results in administration to the microbe. For example, the subject can be a plant or an animal. In certain embodiments, the subject can be a mammal. In certain embodiments, the mammal subject can be a human having and suffering from a microbial infection. In certain embodiments, a combination of an antibiotic and a synthetic amphiphile as disclosed herein is administered in an effective amount. An "effective amount" is that amount, the administration of which to a subject (also referred to as a patient), either in a single dose or as part of a series, is effective for treatment. For example, and effective amount can be an amount that is sufficient to reduce the severity of a microbial infection (or one or more symptoms thereof), ameliorate one or more symptoms of an infection, prevent the advancement of the infection, cause regression of infection, or enhance or improve the therapeutic effect(s) of another therapy. In some embodiments, the effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

In certain embodiments, the antimicrobial agent and the synthetic amphiphile can be administered orally, intravenously, intramuscularly, intraperitoneally, by ointment, cream or any other topical or surface application or surface coating. The antimicrobial agent and synthetic amphiphile can be administered in a single treatment or administered multiple times such as on a schedule or in a series over a period of time. The antimicrobial agent and the synthetic amphiphile can be administered at the same time or practically at the same time, such as immediate sequential administration. In certain embodiments, the antimicrobial agent and the synthetic amphiphile are pre-combined with each other into a composition comprising a combination of antimicrobial agent and synthetic amphiphile. Thus, the antimicrobial could be covalently attached to the hydraphile or lariat ether through an ester linkage which could be cleaved by endogenous esterase or amidase enzymes. In certain embodiments, the antimicrobial agent can be administered first followed by administration of the synthetic amphiphile. In certain embodiments, the synthetic amphiphile can be administered first followed by administration of the antimicrobial agent. The antimicrobial agent is considered to be administered with the synthetic amphiphile so long as both compositions are simultaneously contacted with a microbe even if not simultaneously applied, such as simultaneous in a culture with a microbe, simultaneously on a surface with a microbe, or simultaneously in a subject being treated. In certain embodiments, the simultaneous presence of both the antimicrobial agent and the synthetic amphiphile act together to enhance antimicrobial activity. In certain embodiments, the simultaneous presence of both the antimicrobial agent and the synthetic amphiphile reverse the resistance of a microbe to the anti-microbial agent.

In certain embodiments, the synthetic amphiphile, the antimicrobial agent, or both the synthetic amphiphile and the antimicrobial agent are administered at concentrations below their minimum inhibitory concentration (MIC) values. When certain antimicrobial agents and lariat ethers or certain antimicrobial agents and hydraphiles, one or more at concentrations below their minimum inhibitory concentrations, are co-administered to bacteria in the family Enterobacteriaceae (such as but not limited to *E. coli*), to bacteria in the family Bacillaceae (such as but not limited to *B. subtilis*), and to bacteria in the family Pseudomonadaceae (such as but not limited to *Pseudomonas aeruginosa*), the efficacy of the antibiotic/synthetic amphiphile combination is enhanced by as much as about 30-fold, or by as much as about 48-fold, or greater compared to the activity of either individual component. Efficacious results have been observed in the Gram negative bacterium *Escherichia coli* as the DH5α or K-12 strain. Other strains of *E. coli* are contemplated along with known strains of other Gram negative bacteria such as *Pseudomonas aeruginosa*. Application to Gram positive bacteria including but not limited to *B. subtilis* is also contemplated. Other bacteria and microbes, including but not limited to *Candida albicans, Trichophyton rubrum, Aspergillus, blastomyces, dermatitides, Cryptococcus neoformans, Mycobacterium, Klebsiella, Eniterococcus, Staphylococcus*, and primitive eukaryotes such as yeast, for example *Saccharomyces cerevisiae*, and fungi, are also contemplated herein.

It has also been discovered that synthetic amphiphiles such as, but not limited to, lariat ethers and hydraphiles can be administered with an antimicrobial agent, such as an antibiotic, to organisms resistant to the antimicrobial agent, such that the resistant organism becomes susceptible to the antimicrobial agent. This is referred to herein as reversing the resistance of a microbe to an antimicrobial agent such as reversing the resistance of a bacterium to an antibiotic. As used herein, antibiotic "resistance" or the assertion that an organism is "resistant" to antibiotics means that some part or all of the organism in question does not respond to the antibiotic either by having its growth inhibited or being killed. For example, the tetracycline resistant *E. coli* reported herein were obtained from a commercial supplier and it was found that their MIC was ~900 μM. This compares with the MIC of 12 μM reported in Table 5 for tetracycline against *E. coli*. This means that the tetracycline resistant *E. coli* requires a ~75-fold greater concentration of antibiotic to inhibit growth.

In certain embodiments, the synthetic amphiphile can be a bis(amide) compound having the chemical structure of Formula 5. The size of the macrocyclic ring can range from about 12 members to about 48 members. The side arms can be saturated or unsaturated alkyl, saturated or unsaturated aralkyl, aryl or substituted aryl including heteroaromatic groups. The side arms can possess heteroatoms such as oxygen, nitrogen, and/or sulfur. Heteroatoms can also be present in groups appended to the aryl or heteroaryl residues.

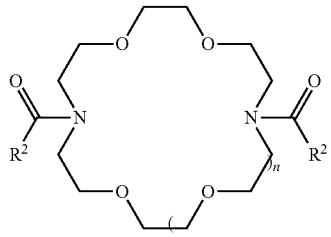

Formula 5

Figure 5:
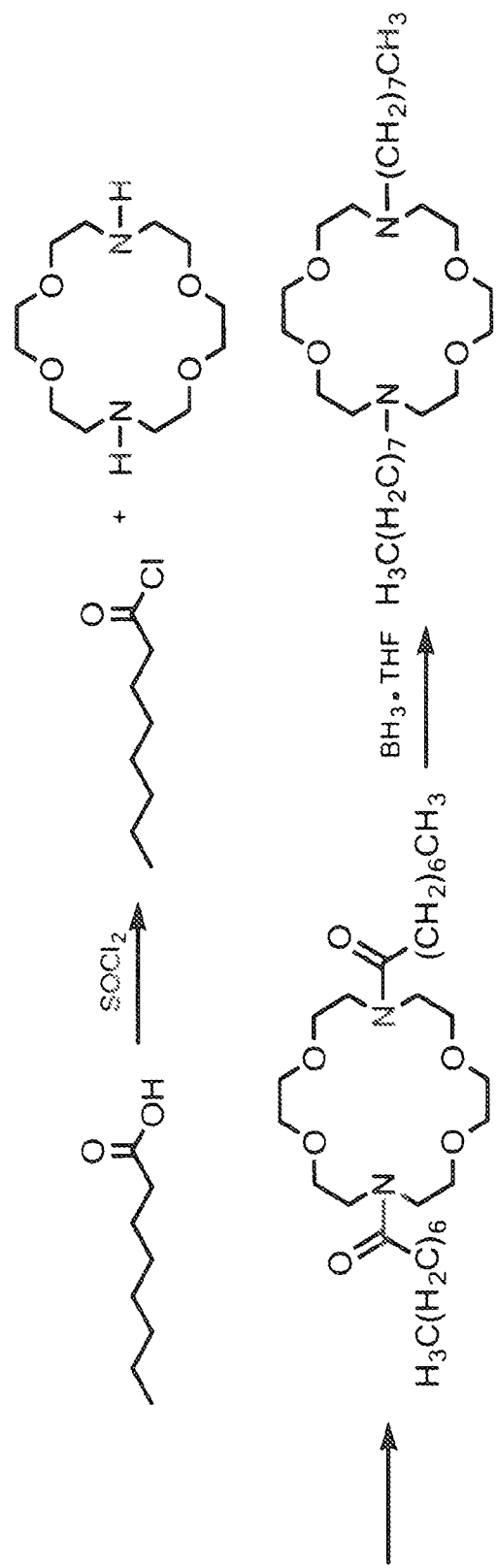
FIG. 5 is a synthetic scheme for the preparation of N,N'-di-n-octyl-4,13-diaza-18-crown-6.

The synthesis of compounds such as N,N'-bis(n-octyl)-4,13-diaza-18-crown-6 and N,N'-bis(n-undecyl)-4,13-diaza-18-crown-6 can readily be accomplished by methods known in the art. An example is to treat 4,13-diaza-18-crown-6 with an alkyl acid chloride such as n-octanoyl chloride, which in turn can be prepared from octanoic acid and a chlorinating agent such as thionyl chloride ($SOCl_2$) or oxalyl chloride (ClCOCOCl). The result of this reaction is a di-tertiary amide that can be reduced, for example, with lithium aluminum hydride ($LiAlH_4$) or borane ($BH_3.THF$). A typical reaction is illustrated in FIG. 5. It is meant to exemplify the synthetic approach and process but not to be in any way limiting.

Figure 13:
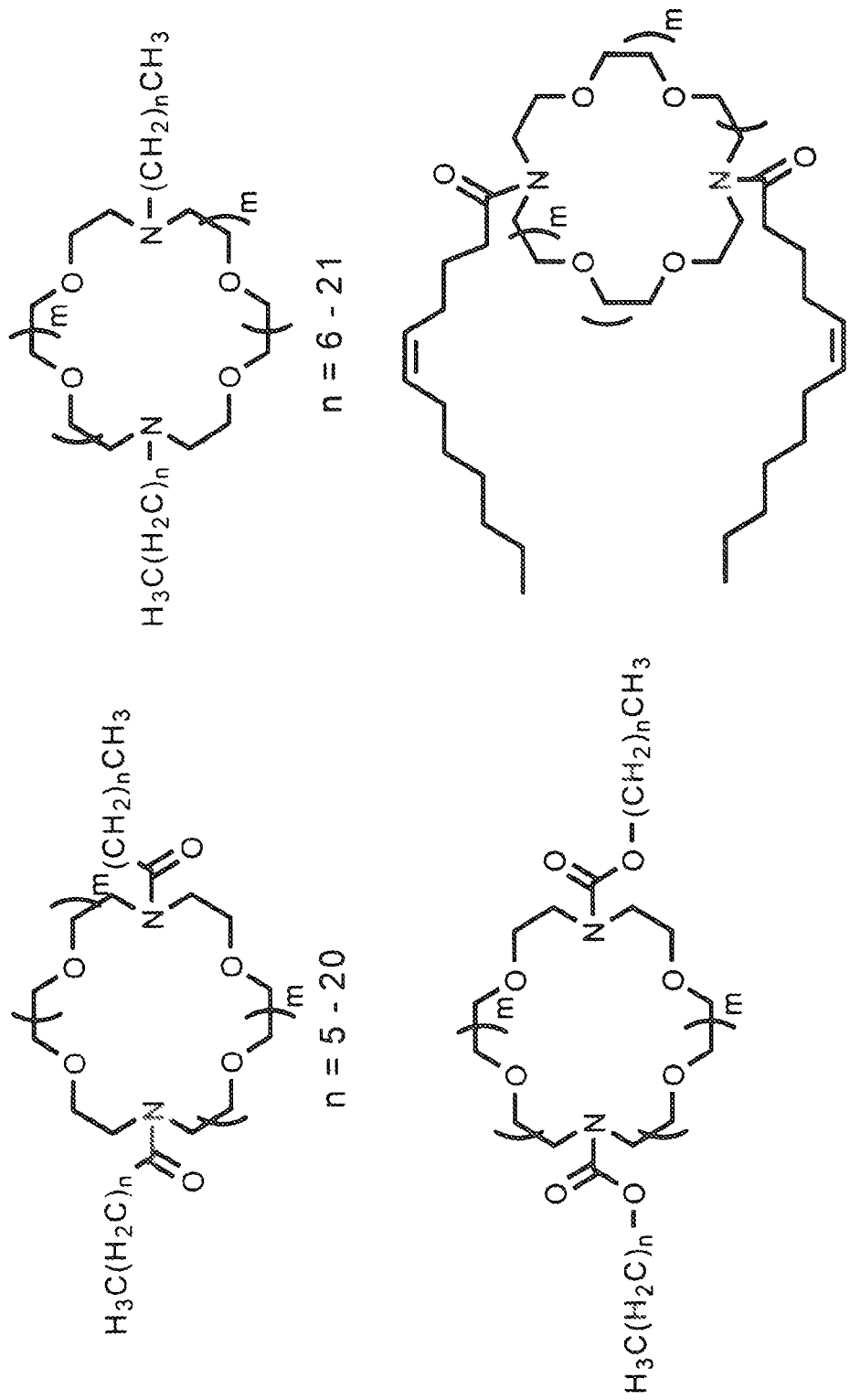
FIG. 13 shows illustrative examples of lariat ether structures that have been prepared.

In certain embodiments, lariat ether compounds can have ring sizes that range from 12 members to 48 members. The side chain substituents shown as $R^1$ or $R^2$ in Formulas 2 and/or 3, can be normal or branched alkyl having from 1-20 carbon atoms, or from 1-22 carbon atoms. These substituents can also be unsaturated, multiply unsaturated, cis and/or trans unsaturated, aralkyl, aromatic, or heteroaromatic. The side arms can possess heteroatoms such as oxygen, nitrogen, and/or sulfur. Heteroatoms can also be present in groups appended to the aryl or heteroaryl residues. Eighteen illustrative structures that have been prepared are shown in FIG. 13.

In certain embodiments, the microbe is *E. coli*, the antibiotic is selected from the group consisting of rifampicin, tetracycline, kanamycin, and erythromycin, and the synthetic amphiphile is N,N'-di-n-octyl-4,13-diaza-18-crown-6 or N,N'-di-n-undecyl-4,13-diaza-18-crown-6. In certain embodiments, the microbe is *E. coli*, the antibiotic is rifampicin, and the synthetic amphiphile is N,N'-di-n-octyl-4,13-diaza-18-crown-6. In certain embodiments, the microbe is *E. coli*, the antibiotic is tetracycline, and the synthetic amphiphile is N,N'-di-n-octyl-4,13-diaza-18-crown-6. In certain embodiments, the microbe is *E. coli*, the antibiotic is rifampicin, and the synthetic amphiphile is N,N'-di-n-undecyl-4,13-diaza-18-crown-6 lariat ether. In certain embodiments, the microbe is *E. coli*, the antibiotics tetracycline, and the synthetic amphiphile is N,N'-di-n-undecyl-4,13-diaza-18-crown-6 lariat ether. In certain embodiments, the microbe is *E. coli*, the antibiotic is kanamycin, and the synthetic amphiphile is N,N'-di-n-undecyl-4,13-diaza-18-crown-6. In certain embodiments, the microbe is *E. coli*, the antibiotic is erythromycin, and the synthetic amphiphile is N,N'-di-n-undecyl-4,13-diaza-18-crown-6.

In certain embodiments, the microbe is a tetracycline resistant strain of *E. coli*, the antibiotic is tetracycline, and the synthetic amphiphile is a hydraphile. In certain embodiments, the microbe is a tetracycline resistant strain of *E. coli*, the antibiotic is tetracycline, and the synthetic amphiphile is benzyl $C_8$ hydraphile. In certain embodiments, the microbe is a tetracycline resistant strain of E. coli, the antibiotic is tetracycline, and the synthetic amphiphile is benzyl $C_{14}$ hydraphile.

The following disclosed embodiments are merely representative. Thus, specific structural, functional, and procedural details disclosed in the following examples are not to be interpreted as limiting.

EXAMPLES

Among the organisms studied are several strains of the bacterium E. coli. These include, but are not limited to, DH5α, JM109, K-12, and tetracycline-resistant E. coli, the latter being an E. coli strain possessing the tet-A efflux pump. Experiments were conducted to determine the MIC values for the synthetic amphiphiles known as lariat ethers according to the procedures described in Antimicrobial M07-A9: Methods for Dilution Antimicrobial Susceptibility Tests for Bacteria that Grow Aerobically; Clinical and Laboratory Standards Institute, 2012; Vol. 32, 67 pp. MIC values so determined for several lariat ethers and for several antibiotics are shown in Table 1.

TABLE 1

Minimum Inhibitory Concentrations for Synthetic Amphiphiles and Antibiotics.

| Antibiotic or $R^1$ in Formula 3 | MIC (µM) | | |
|---|---|---|---|
| | E. coli | B. stubtilis | S. cerevisiae |
| n-octyl | 120 | 105 | 25 |
| n-decyl | 11 | 2.8 | 2.8 |
| n-undecyl | 24 | 9 | 1.5 |
| n-dodecyl | >300 | 2.5 | 2.5 |
| n-tetradecyl | >300 | >300 | >300 |
| n-hexadecyl | >300 | >300 | >300 |
| n-octadecyl | >300 | >300 | >300 |
| erythromycin | >400 | — | — |
| kanamycin | 30 | — | — |
| rifampicin | 60 | — | — |
| tetracycline | 12 | — | — |
| tobramycin | 15 | — | — |

Table 2 shows the effect of combining rifampicin or tetracycline with N,N'-bis(n-octyl)-4,13-diaza-18-crown-6 and then exposing the E. coli to the combination. Note that DMSO is the standard abbreviation for dimethylsulfoxide.

TABLE 2

Combination of $C_8$ lariat ethers and antibiotics against DH5α E. coli

| Side Chain | MIC (µM) | Used (µM) | Antibiotic | MIC (µM) | Used (µM) | vol-% DMSO | Fold Enhancement |
|---|---|---|---|---|---|---|---|
| n-$C_8$ | >120 | 80 | rifampicin | 64 | 3 ± 1 | 0.4 | 21 |
| n-$C_8$ | >120 | 60 | rifampicin | 64 | 3 ± 1 | 0.4 | 21 |
| n-$C_8$ | >120 | 40 | rifampicin | 64 | 3 ± 1 | 0.4 | 21 |
| n-$C_8$ | >120 | 100 | tetracycline | 12 | 0.25 | 0.4 | 48 |
| n-$C_8$ | >120 | 80 | tetracycline | 12 | 0.5 | 0.4 | 24 |
| n-$C_8$ | >120 | 60 | tetracycline | 12 | 2 | 0.4 | 6 |
| n-$C_8$ | >120 | 40 | tetracycline | 12 | 2 | 0.4 | 6 |
| n-$C_8$ | >120 | 30 | tetracycline | 12 | 3 | ≤0.6 | 4 |
| n-$C_8$ | >120 | 20 | tetracycline | 12 | 12 | 0.4 | 0 |

Table 2 also shows the effect of combining tetracycline with N,N'-bis(n-octyl)-4,13-diaza-18-crown-6 and then exposing the E. coli to the combination. The MIC of tetracycline decreases in the presence of DMSO.

Table 3 shows the effect of combining rifampicin or tetracycline with N,N'-bis(n-undecyl)-4,13-diaza-18-crown-6 and then exposing the E. coli to the combination.

TABLE 3

Combination of $C_{11}$ lariat ethers and antibiotics against DH5α E. coli

| Side Chain | MIC (µM) | Used (µM) | Antibiotic | MIC (µM) | Used (µM) | vol-% DMSO | Fold Enhancement |
|---|---|---|---|---|---|---|---|
| n-$C_{11}$ | 24 | 18 | rifampicin | 60 | 3 | 0.4 | 20 |
| n-$C_{11}$ | 24 | 16 | rifampicin | 60 | 6 | 0.4 | 10 |
| n-$C_{11}$ | 24 | 12 | rifampicin | 60 | 6 | 0.4 | 10 |
| n-$C_{11}$ | 24 | 8 | rifampicin | 60 | 15 | 0.4 | 4 |
| n-$C_{11}$ | 24 | 18 | tetracycline | 12 | 1.5 | 0.4 | 8 |
| n-$C_{11}$ | 24 | 16 | tetracycline | 12 | 0.25 | 0.4 | 48 |
| n-$C_{11}$ | 24 | 12 | tetracycline | 12 | 1 | 0.4 | 12 |
| n-$C_{11}$ | 24 | 4 | tetracycline | 12 | 3 | 0.4 | 4 |

Table 4 shows the effect on the K-12 strain of E. coli by combining various N,N'-disubstituted-4,13-diaza-18-crown-6 lariat ethers having side arms possessing six to twelve carbon atoms with either tetracycline or rifampicin.

TABLE 4

Combination of lariat ethers and antibiotics against K-12 E. coli

| Amphiphile | MIC (µM) | Used (µM) | Antibiotic | MIC (µM) | Used (µM) | Fold Enhancement |
|---|---|---|---|---|---|---|
| $C_8$ lariat ether | 300 | 64 | Tetracycline | 6 | 2.5 | ~2 |
| $C_{10}$ lariat ether | 12 | 1.5 | Tetracycline | 6 | 3 | 2 |
| $C_{11}$ lariat ether | 24 | 6 | Tetracycline | 6 | 2.5 | ~2 |
| $C_{12}$ lariat ether | >512 | 16 | Tetracycline | 6 | 3 | 2 |
| $C_6$ lariat ether | >512 | 250 | Rifampicin | 20 | 10 | 2 |
| $C_8$ lariat ether | 300 | 64 | Rifampicin | 20 | 5 | 4 |
| $C_8$ lariat ether | 300 | 32 | Rifampicin | 20 | 10 | 2 |
| $C_{10}$ lariat ether | 12 | 6 | Rifampicin | 20 | 5 | 4 |
| $C_{11}$ lariat ether | 24 | 6 | Rifampicin | 20 | 10 | 2 |

Previous studies of $C_{12}$ lariat ether did not show toxicity to DH5α E. coli cells but the compound was lethal to B. subtilis and to S. cerevisiae at minimum inhibitory concentrations (MICs) of 2.5 µM. The MICs of $C_6$. $C_8$. $C_{10}$. $C_{11}$, and $C_{14}$ lariat ether to DH15α E. coli were determined to be >360 µM, >240 µM, 12 µM, 24 µM and >360 µM respectively. Peak transport activity was observed for $C_{10}$ lariat ether, which was the most toxic compound in the MIC study. Two-armed $C_8$ and $C_{11}$ lariat ethers have also been shown to enhance the efficacy of rifampicin and tetracycline in DH5α E. coli. Here we have performed toxicity studies of lariat ethers to human embryonic kidney HEK-293 cells to determine the selectivity of the lariat ethers between mammalian and bacterial cells.

The toxicity of $C_6$. $C_8$, $C_{10}$. $C_{11}$ and $C_{14}$ lariat ethers to HEK-293 cells was determined by using an MTT assay. Results are presented in FIG. 3, in graphical form for the percent survival of HEK-293 cells in the presence of various concentrations of lariat ethers. The abscissa is a logarithmic scale for the concentrations ranging from 1 µM to 1000 µM (1 mM) used in the experiment. The ordinate represents percent survival of HEK-293 cells. For $C_8$ and $C_{11}$ lariat ether, concentrations equivalent to half MIC to E. coli, i.e. 60 µM and 12 µM respectively, were also tested for toxicity to HEK-293 cells.

FIG. 3 shows the percent survival of HEK-293 in the presence of various concentrations of lariat ethers. The ordinate ranges from 0-100% and records the survival of human embryonic kidney (HEK-293) cells when exposed to concentrations (1 µM to 1 mM) of lariat ethers having linear side arms ranging from six to fourteen carbon atoms.

As seen in FIG. 3, with the increase in concentrations of lariat ethers, the percent survival decreases. HEK-293 cells have 90% survival in the presence of 0.5% DMSO. Hence, the ~90% survival of HEK-293 cells in the presence of 1 µM $C_8$ and $C_{11}$ lariat ethers is attributed to the toxicity of DMSO (within experimental error as reflected in the error bars). $C_{14}$ lariat ether is considered non-toxic even at 1 mM (1000 µM) because 45% survival of HEK-293 is observed.

Figure 4:
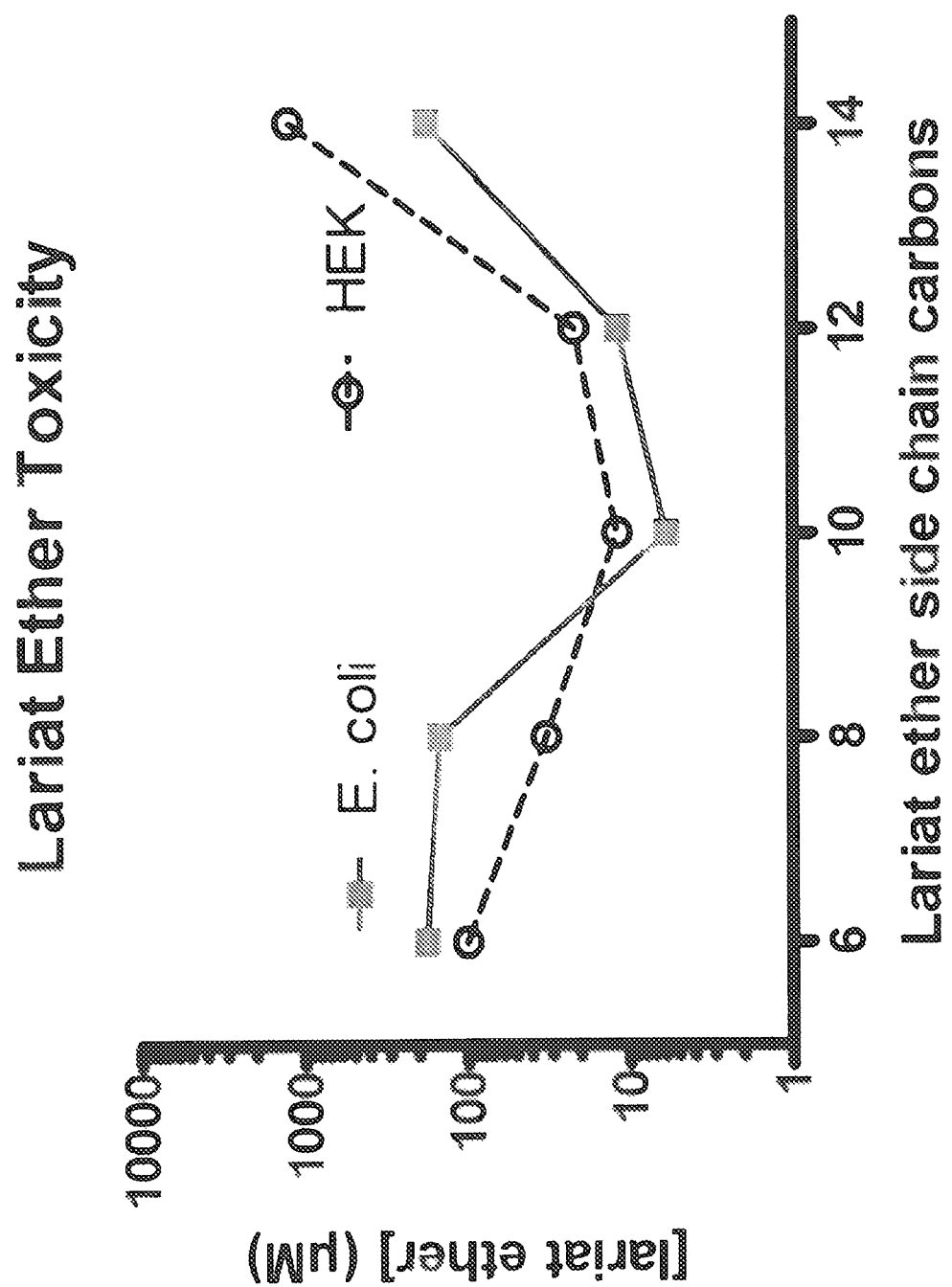
FIG. 4 is a graphical comparison of N,N'-dialkyl-4,13-diaza-18-crown-6 lariat ether toxicity ($LD_{50}$) to *E. coli* and to HEK 293 cells.

Two commonly used abbreviations are $LD_{50}$ and $IC_{50}$. The former is the concentration of an agent that comprises a lethal dose to 50% of the organism under study. The latter is the concentration of agent that inhibits growth of 50% of the organism under study. The data presented and graphed in FIG. 4 represent the averaged (multiple replicates) $LD_{50}$ concentrations of $C_6$, $C_8$, $C_{10}$, $C_{12}$, and $C_{14}$ lariat ethers against HEK-293 cells. It also shows the inhibitory concentration ($IC_{50}$) for each compound to DH5α $E.$ $coli$ cells. The abscissa represents the number of ($CH_2$) groups in spacer chains. The ordinate is logarithmic and reflects the concentrations (in µM) of the various lariat ethers used. The MIC values of $C_6$ and $C_{14}$ lariat ethers are greater than 360 µM but for the purpose of graphical presentation, the $IC_{50}$ values are considered at 180 µM. At 180 µM $C_4$, and $C_{14}$ lariat ethers are inactive against $E.$ $coli$.

FIG. 4 shows the toxicity of various side chain length lariat ethers to HEK-293 and DH5α $E.$ $coli$. In FIG. 4, the open circles (dashed line) represent the average $LD_{50}$ to HEK-293 cells whereas the squares (solid line) represent the $IC_{50}$ to $E.$ $coli$. The $IC_{50}$ for $C_8$ lariat ether to $E.$ $coli$ (150 µM) is much higher than the $LD_{50}$ to HEK-293 (33 µM). The $IC_{50}$ for $C_{11}$ lariat ether to $E.$ $coli$ (12 µM) is lower than the $LD_{50}$ to HEK-293 (22 µM). The synergy experiments for $C_8$ and $C_{11}$ lariat ethers were performed at 60 µM and 12 µM, respectively. In the presence of 60 µM Ca lariat ether, 27% survival of HEK-293 cells was observed. In the presence of 12 µM $C_{11}$ lariat ether, 66% survival of HEK-293 cells was observed. With the increase in side chain length of lariat ethers, the $IC_{50}$ to $E.$ $coli$ is observed to be lower than $LD_{50}$ to HEK-293. This data suggests that with an increase in side chain length, the toxicity of lariat ether to HEK-293 is lower than that to $E.$ $coli$. Similar to the toxicity trend in $E.$ $coli$, $C_{10}$ lariat ether had the highest toxicity to HEK-293.

Minimum inhibitory concentrations were determined using protocols described above for various synthetic amphiphiles and antimicrobials against DH5α, K-12, and tetracycline-resistant strains of $E.$ $coli$. The data are summarized in Table 5. N,N'-Dibenzyl-4,13-diaza-18-crown-6 is referred to in the table as dibenzyldiaza-18-crown-6. The compounds referred to as $C_8$ benzyl hydraphile and $C_{14}$ benzyl hydraphile have the structures shown in Formula 4, in which "n" is 8 and 14, respectively.

Initial studies of hydraphile-enhanced antimicrobial activity were conducted with three hydraphiles. These are illustrated in Formula 4, in which "n"=12, 14, and 16. In several published studies, it was found that hydraphiles having spacer chains [—$(CH_2)_n$—] in the 12-16 range were invariably the most active ion transporters. These results can be found in the following articles: *Chemical Communications* 1998, 2477-2478 and *Journal of Supramolecular Chemistry* 2001, 1, 23-30. It was discovered that hydraphiles that successfully formed ion channels in membranes also killed $E.$ $coli$, as reported in the *Journal of the American Chemical Society* 2002, 124, 9022-9023. In this report, the hydraphile having —$(CH_2)_8$— spacers did not exhibit toxicity to $E.$ $coli$, whereas the benzyl $C_{12}$ hydraphile having —$(CH_2)_2$— spacers killed the bacteria.

All previous studies, both biophysical and biological, indicated that hydraphiles of the general type shown in Formula 4 would be inactive on their own or as adjuncts to antimicrobial agents if their spacer chains [—$(CH_2)_n$—] contained 8 or fewer methylene groups. It was unexpectedly discovered that the short hydraphile benzyl $C_8$ significantly enhanced the potency of several antibiotics.

Studies with a tetracycline-resistant strain of $E.$ $coli$, specifically tetracycline-resistant JM109, have shown that lariat ethers produce significant enhancements of antimicrobial potency. A JM109 strain that is highly resistant to the antibiotic tetracycline was studied in the presence of various lariat ethers at different concentrations. As shown by the data in Table 6, the antimicrobial resistance was reversed. Table 5 shows the results for the tetracycline-resistant JM109 strain of $E.$ $coli$ in the presence of lariat ethers.

TABLE 5

MIC values for synthetic amphiphiles or antimicrobials against tetracycline resistant $E.$ $coli$

| Amphiphile | Antimicrobial | MIC (µM) |
| --- | --- | --- |
| $C_8$ hydraphile | None | 250 ± 10 |
| $C_{10}$ hydraphile | None | 35 ± 5 |
| $C_{12}$ hydraphile | None | 5 ± 0.5 |
| $C_{14}$ hydraphile | None | 2 ± 0.125 |
| $C_6$ lariat ether | None | >512 |
| $C_8$ lariat ether | None | 120 |
| $C_{10}$ lariat ether | None | 16 |
| $C_{11}$ lariat ether | None | 24 |
| $C_{12}$ lariat ether | None | >512 |
| None | Tetracycline | 900 ± 50 |
| None | Ampicillin | >1000 |

Studies with several strains of $E.$ $coli$ have shown that lariat ethers produce significant enhancements of antimicrobial potency. In particular, a study of tetracycline-resistant $E.$ $coli$ showed that in the presence of lariat ethers, the antimicrobial resistance was reversed. Data are shown in Table 6 for treatment with lariat ethers and tetracycline of tetracycline-resistant strains of $E.$ $coli$.

TABLE 6

Combination of lariat ether and tetracycline against tetracycline resistant $E.$ $coli$

| Amphiphile | MIC (µM) | Used (µM) | Antibiotic | MIC (µM) | Used (µM) | Fold Enhancement |
| --- | --- | --- | --- | --- | --- | --- |
| $C_6$ lariat ether | >512 | 192 | Tetracycline | 900 | 413 | 2 |
| $C_8$ lariat ether | 120 | 80 | Tetracycline | 900 | 87 | 10 |
| $C_8$ lariat ether | 120 | 60 | Tetracycline | 900 | 175 | 5 |
| $C_8$ lariat ether | 120 | 40 | Tetracycline | 900 | 233 | 4 |
| $C_{10}$ lariat ether | 16 | 6 | Tetracycline | 900 | 225 | 4 |
| $C_{10}$ lariat ether | 16 | 9 | Tetracycline | 900 | 56 | 16 |
| $C_{11}$ lariat ether | 24 | 18 | Tetracycline | 900 | 87 | 10 |
| $C_{11}$ lariat ether | 24 | 16 | Tetracycline | 900 | 87 | 10 |
| $C_{11}$ lariat ether | 24 | 12 | Tetracycline | 900 | 87 | 10 |
| $C_{11}$ lariat ether | 24 | 8 | Tetracycline | 900 | 175 | 5 |
| $C_{12}$ lariat ether | >512 | 192 | Tetracycline | 900 | 450 | 2 |

Studies with several strains of $E.$ $coli$ have shown that hydraphiles produce significant enhancements of antimicrobial potency. In particular, a study of tetracycline-resistant $E.$ $coli$ showed that in the presence of hydraphiles, the antimicrobial resistance was reversed. Data are shown in Table 7 for treatment with hydraphiles and tetracycline of tetracycline-resistant strains of *E. coli*.

TABLE 7

Combination of hydraphile and tetracycline against tetracycline resistant *E. coli*

| Amphiphile | MIC (μM) | Used (μM) | Antibiotic | MIC (μM) | Used (μM) | Fold Enhancement |
|---|---|---|---|---|---|---|
| $C_8$ hydraphile | 250 | 125 | Tetracycline | 900 | 30 | 30 |
| $C_8$ hydraphile | 250 | 62.5 | Tetracycline | 900 | 82 | 11 |
| $C_{10}$ hydraphile | 35 | 17.5 | Tetracycline | 900 | 40 | 23 |
| $C_{10}$ hydraphile | 35 | 8.75 | Tetracycline | 900 | 200 | 5 |
| $C_{12}$ hydraphile | 5 | 2.5 | Tetracycline | 900 | 55 | 16 |
| $C_{12}$ hydraphile | 5 | 1.25 | Tetracycline | 900 | 400 | 2 |
| $C_{14}$ hydraphile | 2 | 1 | Tetracycline | 900 | 220 | 4 |
| $C_{14}$ hydraphile | 2 | 0.5 | Tetracycline | 900 | 360 | 3 |

The synthetic amphiphile shown as Compound 6 in FIG. 10 was examined with two *E. coli* strains: K-12 and the tetracycline resistant strain. In the presence of tetracycline and in the absence of a synthetic amphiphile, the MIC values against K-12 and the tetracycline resistant strain were 6 μM and 900 μM, respectively. For the K-12 strain, addition of Compound 6 in FIG. 10 at a concentration of approximately half its MIC, in the presence of tetracycline, altered the MIC of tetracycline from 6 μM to 2 μM. This is an approximately three-fold increase in efficacy. For the tetracycline-resistant strain, addition of compound 6 in FIG. 10 at a concentration of approximately half its MIC, in the presence of tetracycline, altered the MIC of tetracycline from 900 μM to 150 μM. This is an approximately six-fold increase in efficacy.

Figure 6:
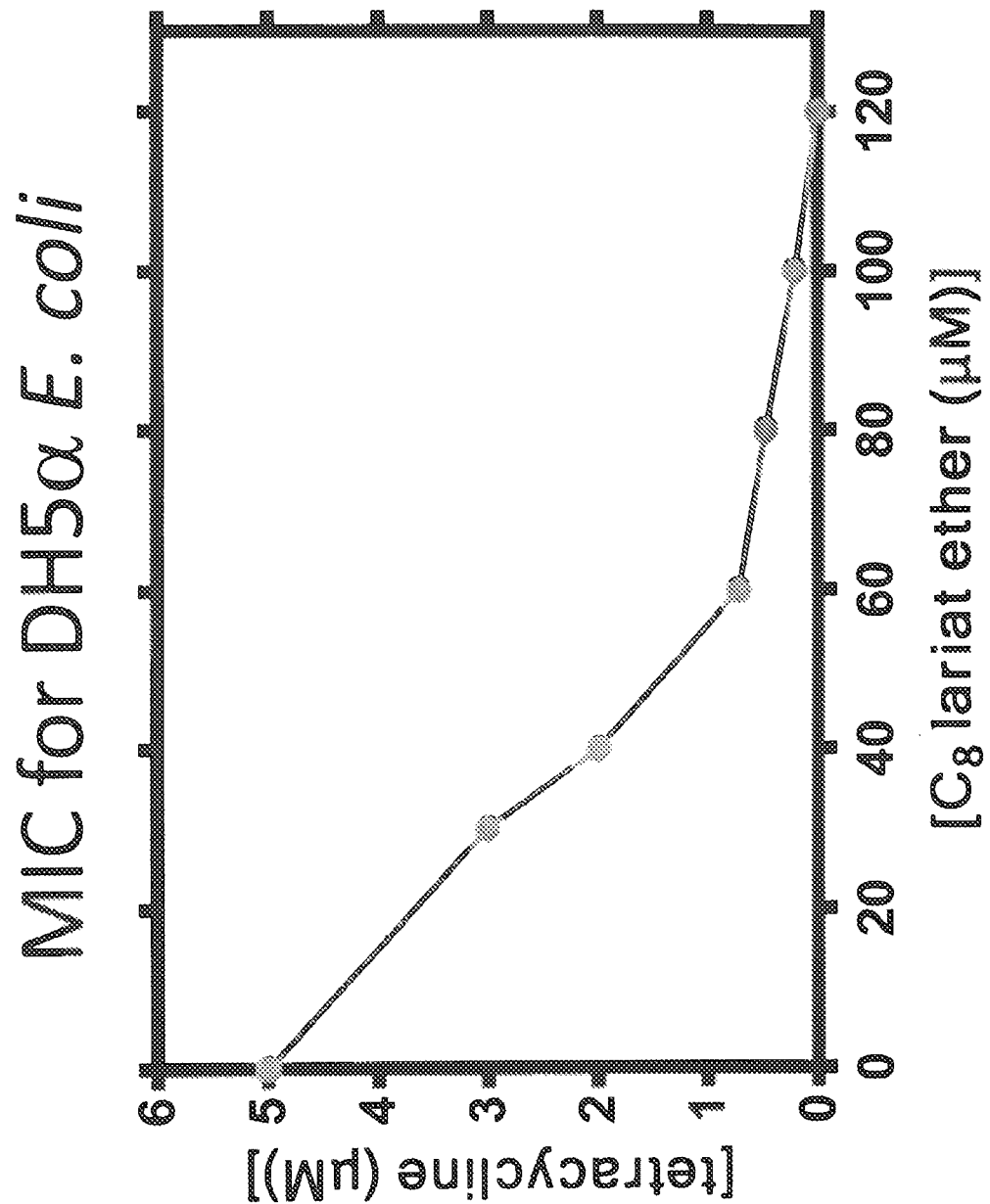
FIG. 6 is a graph showing the relationship between the concentrations of synthetic amphiphile and antibiotic required to inhibit the growth of DH5α *E. coli* treated with $C_8$ lariat ether and tetracycline.
Figure 7:
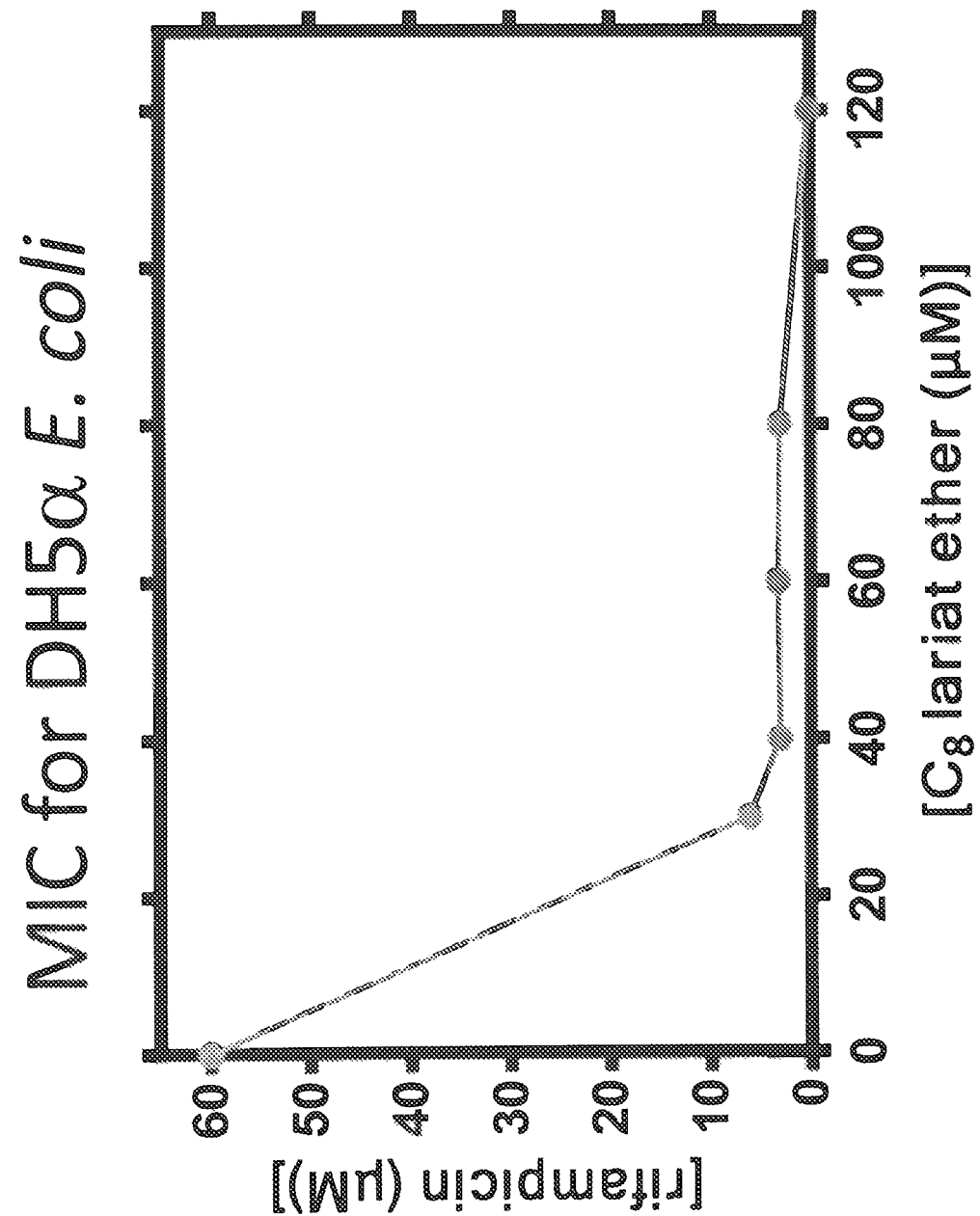
FIG. 7 shows the minimum inhibitory concentration (MIC) for DH5α *E. coli* treated with $C_8$ lariat ether and rifampicin when treated with various concentrations of amphiphile and antibiotic.
Figure 8:
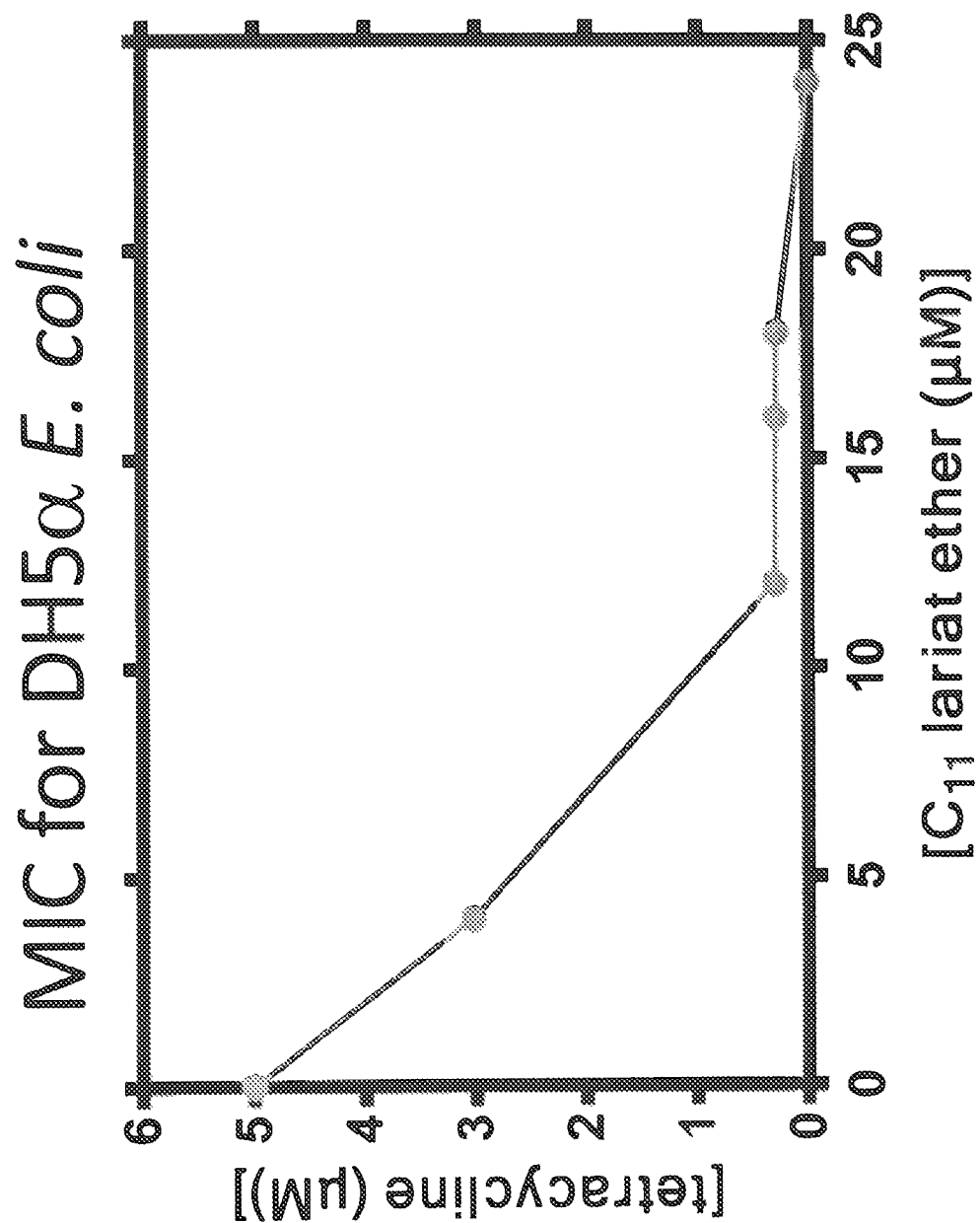
FIG. 8 shows the minimum inhibitory concentration (MIC) for DH5α *E. coli* treated with $C_{11}$ lariat ether and tetracycline when treated with various concentrations of synthetic amphiphile and antibiotic.
Figure 9:
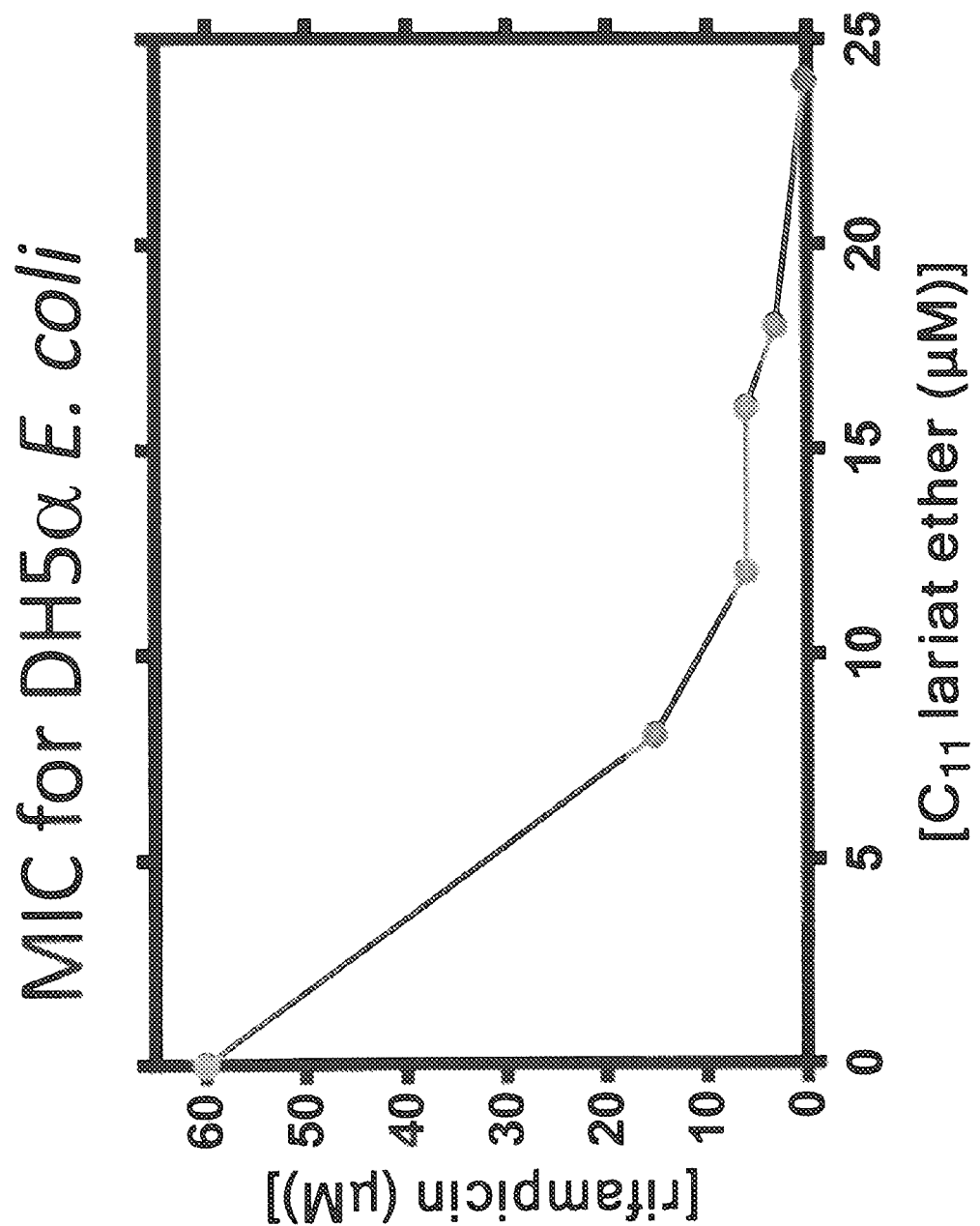
FIG. 9 shows the minimum inhibitory concentration (MIC) for DH5α E. coli treated with $C_{11}$ lariat ether and rifampicin when treated with various concentrations of synthetic amphiphile and antibiotic.

Referring to FIGS. 6 through 9 which show plots of antibiotic concentration as a function of lariat ether concentration for the antibiotics tetracycline and rifampicin with $C_8$ and $C_{11}$ lariat ethers. FIG. 6 is a graph showing the relationship between the concentrations of synthetic amphiphile and antibiotic required to inhibit the growth of *E. coli* treated with $C_8$ lariat ether and tetracycline. FIG. 7 is a graph showing the relationship between the concentrations of synthetic amphiphile and antibiotic required to inhibit the growth of *E. coli* treated with $C_8$ lariat ether and rifampicin. FIG. 8 is a graph showing the relationship between the concentrations of synthetic amphiphile and antibiotic required to inhibit the growth of for *E. coli* treated with $C_{11}$ lariat ether and tetracycline. FIG. 9 is a graph showing the relationship between the concentrations of synthetic amphiphile and antibiotic required to inhibit the growth of *E. coli* treated with $C_{11}$ lariat ether and rifampicin. Graphical representations are known to those in the art as a means to assess whether a combination of drugs is additive or synergistic as described in *Drug Synergism and Dose-Effect Data Analysis*; Chapman & Hall: Boca Raton, 2000, 267 pp.

Example 1. N,N'-Di-n-octyl-4,13-diaza-18-crown-6

This compound was prepared by methods known in the art. 4,13-Diaza-18-crown-6 was acylated with octanoyl chloride and the resulting diamide was reduced with $B_2H_6$.THF. Short path distillation afforded the lariat ether (63%) as a colorless oil (bp 181-190° C., 0.04 torr).

Example 2. Determination of Minimum Inhibitory Concentrations

Minimal Inhibitory Concentration (MIC) Procedure. The steps used in the experimental determination of the minimum inhibitory concentration (MIC) are recorded below.

1. Streak the *E. coli* (DH5α or K-12 MG 655) strain on L.B agar plates. For tetracycline resistant *E. coli* use L.B. agar+ampicillin plates (150 μM).
2. Inoculate a 2 ml of L.B. Miller media with one colony of bacteria and incubate overnight at 37° C. and 200 rpm. For tetracycline resistant *E. coli*, use 128 μM ampicillin in L. B. Miller media.
3. Prepare an excel file outlining the concentrations and volumes of compound and L.B. Miller media required to be added to each test tube. Note: The total volume of media is 2000 μL in each test tube.
4. Prepare initial concentration of all the compounds required.
5. Dilute from the initial concentration according to the required concentration of the compound. Note: For compounds that are dissolved in DMSO, dilutions must be made in a way that the volume of DMSO added to each test tube is kept constant at 5 μL (0.25% by volume). For compounds that are dissolved in water, the volume of water added to media is constant at 5 μL (0.25% by volume).
6. Add the appropriate volume of media to each test tube.
7. In a separate test tube, knock back *E. coli* to optical density (A=600 nm. O.D.)=0.100 by adding 50 μL of *E. coli* to 1950 μL of L.B. Miller media. Check O.D. every 30 minutes until the *E. coli* grows to O.D.=0.600.
8. While the *E. coli* grows, add the appropriate volume of compound to each test tube.
   Vortex each test tube for 2-3 seconds.
9. Add 20 μL *E. coli* grown to O.D.=0.600 to each sample. Note: Manage experiments so that *E. coli* is grown to O.D.=0.600 before adding to each test tube.
10. Vortex each test tube for 2-3 seconds.
11. Inoculate test tubes at 37° C. and 200 RPM for 24 hours.
    Results are determined by visual verification or O.D. (λ=600 nm) measurement of the growth or no growth of bacteria.

Example 3

This study was conducted with N,N'-di-n-octyl-4,13-diaza-18-crown-6 ($C_8$ lariat ether). A stock solution was prepared at a concentration of 20 mM in DMSO. A tetracycline stock solution was prepared at a concentration of 1 mM in Milli-Q $H_2O$. An 80 μM solution of $C_5$ lariat in media was prepared by adding 8 μL of $C_8$ lariat stock solution (20 mM) to 2 mL media. Preparation of 60 μM, 40 μM, and 20 μM solutions of $C_8$ lariat, 6 μL, 4 μL, and 2 μL of $C_8$ lariat stock solution (20 mM) was added to 2 mL media respectively and to make the volume of DMSO the same (0.4 vol-% with respect to media) appropriate volume of DMSO was added (2, 4, and 6 of μL DMSO respectively).

Example 4. Co-Administration of Antibiotics and Lariat Ethers to *E. coli*. $C_8$ Lariat (MIC=120 μM) and Tetracycline Against *E. coli* DH5α (MIC=10 μM)

Each concentration of $C_8$-lariat was tested with different concentrations of tetracycline (from 6 μM to 0.25 μM). Tetracycline was dissolved in water. The volume of water added was between 12 to 0.5 μL. The volume of water added was not constant but the volume of media was changed so that the total volume was kept constant at 2 mL.

Example 5. Procedure for the Assessment of Potential Antibiotic Synergy

1. Steps 1-7, described in the MIC procedure, shown in Example 2, were followed.
2. While the *E. coli* grew, the appropriate volume of compound was added to each test tube.
3. Antibiotics were added at the required volume of solution to obtain the desired concentration in each test tube. The concentration of each compound was adjusted so that the total volume of DMSO added to each test tube was 5 μL (0.25% by volume with respect to final volume i.e. 2000 μL. i.e. 2 mL).
4. Each test tube was vortexed for 2-3 seconds.
5. Steps 10-12 from the MIC procedure, shown in Example 2, were then executed.

Example 6. Determination of Toxicity of Lariat Ethers to HEK-293 and *E. coli* Cells Growth medium containing DMEM with high glucose (ATCC). 10% fetal bovine serum (FBS: Sigma-Aldrich) and 10 μg/mL of blasticidin (Thermo-Fischer) was prepared. HEK 293 cells were thawed out from cryo-preserved samples in 10 mL growth media, centrifuged at 500 rpm for 10 minutes to remove preservative. The cells were then resuspended in fresh growth medium and cultured using a T-75 flask (Thermo-Fischer) at 37° C. and 5% $CO_2$. Cells were monitored for confluence and growth medium was replaced every 48 h, until cells were placed onto a 96-well plate for toxicity studies.

After reaching 80-90% confluence, cells were trypsinized and suspended in media containing DMEM and 10% FBS (no antibiotics). The cells were counted on a hemacytometer and plated at a density of 20,000 cells per well in a 96-well plate and grown for 24 hours to reach 60-70% confluence. DMSO stocks of $C_6$, $C_8$, $C_{10}$, $C_{11}$ and $C_{14}$ diaza-18-crown-6 lariat ethers were prepared at 200 mM and diluted 1:10 to get working concentrations of 20 mM, 2 mM, and 0.2 mM. Each stock was further diluted 1:100 into DMEM supplemented with 10% FBS to get final concentrations of 1 mM, 0.1 mM, 0.01 mM (10 μM) and 0.001 mM (1 μM). The original media was then removed from the cells and replaced with 200 μL media containing the desired concentration of compound. Three wells were used for each concentration providing experimental triplicates. As a positive control for growth, three wells containing cells were treated with DMEM supplemented with 10% FBS. For DMSO control, three wells containing cells were treated with DMEM supplemented with 10% FBS and 0.5% DMSO. As a negative control, wells without cells were treated with DMEM supplemented with 10% FIBS and 0.5% DMSO. The 96-well plate was then returned to 37° C. and 5% $CO_2$ for 24 hours. After incubation. MTT assay (Sigma-Aldrich) was performed according to manufacturer's protocol. The absorbance was measured at 570 nm and nonspecific absorbance was corrected at 650 nm, using SpectraMax340 micro plate reader.

The experiment was performed in triplicate and the average of percent survival of three experiments was determined. The graph in FIG. 3 represents the percent survival with increasing concentration of lariat ethers on a logarithmic scale. The error bars represent the standard error. The lethal dose 50 ($LD_{50}$) for each compound was calculated by using the equation for a logarithmic regression curve. The $R^2$ value for each curve was approximately 0.9.

What is claimed is:

1. A method of enhancing the antimicrobial activity of an antibiotic, the method comprising administering the antibiotic with a synthetic amphiphile to a bacterium that is resistant to the antibiotic,
wherein the synthetic amphiphile comprises the general Formula 3:

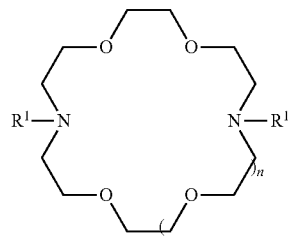

Formula 3 wherein n is 1 and $R_1$ is a $C_8$-$C_{12}$ linear alkyl,
wherein the synthetic amphiphile is administered at a concentration of half or less of its minimum inhibitory concentration (MIC) against the antibiotic resistant microbe as determined in the absence of the antibiotic,
wherein the antibiotic is tobramycin or tetracycline, and
wherein the antimicrobial activity of the antibiotic is increased by at least 10-fold by administration with the synthetic amphiphile.

2. The method of claim 1, wherein the antibiotic is also administered at a concentration lower than its minimum inhibitory concentration (MIC) against the antibiotic resistant microbe as determined in the absence of the synthetic amphiphile.

3. The method of claim 1, wherein the synthetic amphiphile is administered as an aggregate of amphiphiles or a mixture of amphiphiles with a pharmaceutically acceptable solvent or solvent system.

4. The method of claim 1, wherein the antibiotic and the synthetic amphiphile are administered in a liposome.

5. The method of claim 1, wherein the antibiotic and the synthetic amphiphile have formed a salt.

6. The method of claim 1, wherein the antibiotic and the synthetic amphiphile are each administered in a salt form.

7. The method of claim 1, wherein the bacterium is in the family Enterobacteriaceae, in the family Bacillaceae, in the family Staphylococcaceae, or in the family Pseudomonadaceae.

8. The method of claim 1, wherein the bacterium is *E. coli*.

9. The method of claim 8, wherein the bacterium is a tetracycline resistant strain of *E. coli* and the antibiotic is tetracycline.

10. The method of claim 1, wherein the synthetic amphiphile is in a salt form by protonation or alkylation at nitrogen.

11. The method of claim 1, wherein the resistance of the bacterium to the antibiotic is reversed.

* * * * *